US010260101B2

(12) United States Patent
Bastian et al.

(10) Patent No.: US 10,260,101 B2
(45) Date of Patent: Apr. 16, 2019

(54) C-KIT ONCOGENE MUTATIONS IN MELANOMA

(71) Applicant: The Regents of the University of California, Oakland, CA (US)

(72) Inventors: Boris C. Bastian, Mill Valley, CA (US); John A. Curtin, Manchester (GB)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/055,752

(22) Filed: Oct. 16, 2013

(65) Prior Publication Data

US 2014/0045182 A1    Feb. 13, 2014

Related U.S. Application Data

(63) Continuation of application No. 12/090,855, filed as application No. PCT/US2006/041510 on Oct. 23, 2006, now abandoned.

(60) Provisional application No. 60/729,171, filed on Oct. 21, 2005.

(51) Int. Cl.
    *C12Q 1/68*      (2018.01)
    *C12Q 1/6886*    (2018.01)

(52) U.S. Cl.
    CPC ..... *C12Q 1/6886* (2013.01); *C12Q 2600/106* (2013.01); *C12Q 2600/118* (2013.01); *C12Q 2600/156* (2013.01)

(58) Field of Classification Search
    None
    See application file for complete search history.

(56) References Cited

U.S. PATENT DOCUMENTS

| 2003/0083485 A1 * | 5/2003 | Milos et al. ........... 536/23.2 |
| 2004/0005623 A1   | 1/2004 | Longley |
| 2005/0064440 A1   | 3/2005 | Roth et al. |

FOREIGN PATENT DOCUMENTS

WO    03/001985 A2    1/2003

OTHER PUBLICATIONS

Kim et al. British J Cancer. Aug. 2008. 99(5): 734-740.*
Beghini et al The Hematology J. 2002. 3: 157-163.*
Skin Cancer Foundation. "Types of Melanoma", available via url < skincancer.org/skin-cancer-information/melanoma/types-of-melanoma> printed on Nov. 14, 2016.*
Landi et al Science. Jun. 29, 2006. 313 (5786): 521-522 and Supporting Online Material p. 1-13.*
The International Search Report from PCT/US2006/041510, dated May 17, 2007.
The Supplemental European Search Report from EP 06836496.7, dated May 6, 2010.
Communication Pursuant to Article 94(3) EPC from from EP 06836496.7, dated Jul. 8, 2013.
Notice of Reasons for Rejection from JP Appl. No. 2008-536616, dated Feb. 23, 2012. 4 pages. English translation version.
Notice of Reasons for Rejection from JP Appl. No. 2008-536616, dated May 20, 2013. 3 pages. English translation version.
All-Ericsson et al., "c-Kit-Dependent Growth of Uveal Melanoma Cells: A Potential Therapeutic Target?," 2004, *Investigative Ophthalmology & Visual Science*, vol. 45(7), pp. 2075-2082.
Anticancer agent (monoclonal antibody), KW-2871, has entered clinical Phase I/ early Phase II study in the US., Kyowa Hakko News Releases, Jun. 10, 2002, retrieved on May 13, 2013, URL, http://www.kyowa-kirin.com/news_release/kyowa/2002/er020610.html.
Beadling et al., "KIT gene mutations and copy number in melanoma subtypes," 2008, *Clin. Cancer Res.*, vol. 14, pp. 8621-8628.
Bentires-Alj et al., "Activating mutations in Noonan Syndrome-associated SHP2/PTPN11 gene in human solid tumors and adult acute myelogenous leukemia," 2004, *Cancer Research*, vol. 64, pp. 8816-8820.
Blanco et al., "Detection of circulating malignant cells in a uveal melanoma animal model," 2004, *Proc Amer Assoc Cancer Res.*, vol. 45, Abstract #5110.
Boaziz C:A28 "[Contribution of a new nitrosourea compound: fotemustine].", Pathologie-Biologie Dec. 1992, vol. 40, No. 9 Pt 2, Dec. 1992 (Dec. 1992), pp. 964-968, XP009170664, ISSN: 0369-8114 A35.
Boissan et al., "c-Kit and c-kit mutations in mastocystosis and other hematological diseases," 2000, *J. Leukoc. Biol.*, vol. 67, pp. 135-148.
Curtin et al., "Distinct sets of genetic alterations in melanoma," 2005, *The New England Journal of Medicine*, vol. 353(20), pp. 2135-2147; with Supplementary Appendix (10 pages).
Eton et al., "Phase II trial of imatinib mesylate (STI-571) in metastatic melanoma (MM)," 2004, *Journal of Clinical Oncology*, vol. 22, No. 14S, 7528.
GeneCards®, "v-kit Hardy-Zuckerman 4 feline sarcoma viral oncogene homolog," accessed Aug. 3, 2010. URL <genecards.org/cgibin/carddisp.pl?gene=KIT&snp=181&rf=/home/genecards/currentlwebsite/carddisp.pl#snp>.
Halushka et al., "Patters of single-nucleotide polymorphisms in candidate genes for blood-pressure homeostasis," 1999, *Nature Genetics*, vol. 22, pp. 239-247.
Heinrich et al., "Inhibition of KIT tyrosine kinase activity: A novel molecular approach to the treatment of KIT-positive malignancies," 2002, *Journal of Clinical Oncology*, vol. 20(6), pp. 1692-1703.
Helmke et al., "Mutations of the KIT gene and KIT (CD117) protein expression in anorectal melanoma," 2005, *Molecular Pathology*, vol. 201, p. 239, poster 216 available online Apr. 18, 2005.
Hirschhorn et al., "A comprehensive review of genetic association studies," 2002, *Genetics in Medicine*, vol. 4(2), pp. 45-61.
Huang et al., "Enforced c-KIT expression renders highly metastatic human melanoma cells susceptible to stem cell factor-induced apoptosis and inhibits their tumorigenic and metastatic potential," 1996, *Oncogene*, vol. 13(11), pp. 2339-2347.

(Continued)

*Primary Examiner* — Carla J Myers

(74) *Attorney, Agent, or Firm* — Kilpatrick Townsend & Stockton LLP

(57) ABSTRACT

The present invention provides methods of detecting c-KIT-dependent-melanoma for diagnostic and prognostic purposes. The invention further provides methods of treating such melanoma by inhibiting c-KIT.

4 Claims, 4 Drawing Sheets

Specification includes a Sequence Listing.

(56) References Cited

OTHER PUBLICATIONS

Ioannidis et al., "Replication validity of genetic associate studies," 2001 *Nature Genetics*, vol. 29, pp. 306-309. ePub Oct. 15, 2001.
Lassam, N. and S. Bickford, "Loss of c-kit expression in cultured melanoma cells," 1992, *Oncogene*, vol. 7(1), pp. 51-56.
Lucentini, J., "Gene association studies typically wrong," 2004, *The Scientist*, vol. 18, p. 20.
Montone et al., "Proto-oncogene c-kit expression in malignant melanoma: protein loss with tumor progression," 1997, *Modern Pathology*, vol. 10(9), pp. 939-944.
Natali et al., "Progression of human cutaneous melanoma is associated with loss of expression of c-kit proto-oncogene receptor," 1992, *International Journal of Cancer*, vol. 52(2), pp. 197-201.
Ngo et al., "Computational Complexity, Protein Structure Predictio and the Levinthal Paradox," Chapter 14 of *The Protein Folding Problem and Tertiary Structure Prediction*, 1994, Mertz et al (ed). Birkhauser, Boston, MA, pp. 433 and 492-495.
Ohashi et al., "c-Kit receptor expression in cutaneous malignant melanoma and benign melanotic naevi," 1996, *Melanoma Research*, vol. 6(1), pp. 25-30.
Özgüro et al., "Anorectal melanoma metastatic to the breast," 1999 *Clinical Gastroenterology*, vol. 29(2), pp. 197-199.
Pache et al., "Sequence analysis and high-throughput immunohistochemical profiling of KIT (CD117) expression in uveal melanmoa using tissue microarrays," 2003, *Virchows. Arch.*, vol. 443, pp. 741-744.
Pereira et al., "The role of c-kit and imatinib mesylate in uveal melanoma," 2005, *The Journal of Carcinogenesis*, vol. 4(19), pp. 1-8.
Potti et al., "Immunohistochemical determination of HER-2/neu overexpression in malignant melanoma reveals no prognostic value, while c-Kit (CD117) overexpression exhibits potential therapeutic implications," 2003, *The Journal of Carcinogenesis*vol. 2, pp. 1-7.
Skolnick et al., "From genes to protein structure and function: novel applications of computational approaches to the genomic era," 2000, *Trends in Biotechnology*, vol. 18(1 ), pp. 34-39.
Stefanou et al, "Immunohistochemical expression of vascular endothelial growth factor (VEGF) and C-KIT in cutaneous melanocytic lesions," 2004, *International Journal of Surgical Pathology*, vol. 12(2), pp. 133-138.
Unknown: "Phase III randomized study of fotemustine administered as an intravenous infusion versus an intra-arterial hepatic perfusion in patients with surgically incurable or unresectable liver metastases secondary to uveal melanoma", , Sep. 9, 2005 (Sep. 9, 2005). Retrieved from the Internet: URL: <clinicaltrials.gov/archive/NCT00110123/2005_09_09>.
Wacholder et al., "Asessing the probability that a positive report is false: an approach for molecular epidemiology studies," 2004, *J. Natl. Cancer Inst.*, vol. 96(6), pp. 434-444.
Went et al., "Prevalence of KIT expression in human tumors," 2004 *Journal of Clinical Oncology*, vol. 22(22), pp. 4514-4522.
Whisstock et al., "Prediction of protein function from protein sequence and structure," 2003, *Quarterly Reviews of Biophysics*, vol. 36, pp. 307-340.
Willmore-Payne et al., "Human malignant melanoma: detection of BRAF- and c-kit-activating mutations by high-resolution amplicon melting analysis," 2005, *Human Pathology*, vol. 36, pp. 486-493.
Zakut et al., "KIT ligand (mast cell growth factor) inhibits the growth of KIT-expressing melanoma cells," 1993, *Oncogene*, vol. 8(8), pp. 2221-2229.

* cited by examiner

C-KIT ONCOGENE MUTATIONS IN MELANOMA

CROSS-REFERENCE TO RELATED APPLICATIONS

This application is a continuation of U.S. application Ser. No. 12/090,855, filed Apr. 18, 2008, which is a national phase application under 35 U.S.C. § 371 of International Application No. PCT/US2006/041510, filed Oct. 23, 2006, which claims priority benefit of U.S. patent application No. 60/729,171, filed Oct. 21, 2005, each of which application is herein incorporated by reference.

STATEMENT AS TO RIGHTS TO INVENTIONS MADE UNDER FEDERALLY SPONSORED RESEARCH OR DEVELOPMENT

This invention was made with Government support under grant no. CA95300 awarded by the National Institutes of Health. The Government has certain rights in this invention.

REFERENCE TO A "SEQUENCE LISTING" SUBMITTED AS AN ASCII TEXT FILE

This application contains a Sequence Listing as a text file named "SEQTXT_81906-890888-165920US.txt" created Oct. 15, 2013, and containing 26,788 bytes. The material contained in this text file is incorporated by reference in its entirety for all purposes.

BACKGROUND OF THE INVENTION

Among melanomas affecting the skin, there is marked variation of histopathology and clinical characteristics, partially depending on anatomic site and sun-exposure patterns. It has recently been shown (Curtin, et al., *New Engl. J. Med.* 353:2135-2147, 2005) that the MAP-kinase and PI3 kinase pathways are activated differently among subtypes of melanoma when tumors are classified according to a combination of UV exposure and anatomic site. Most prominently, while BRAF mutations are highly prevalent (59%) in melanomas occurring on skin without signs of chronic sun-induced damage (non-CSD melanomas), the frequency is very low in melanomas that occur on the palms, soles or subungual sites (acral or mucosal). BRAF mutations are also uncommon in melanomas that occur on skin showing evidence of chronic sun-induced damage (CSD melanomas). About 10 to 20% of melanomas of all subtypes activate these pathways by mutation of NRAS, but mutations of both NRAS and BRAF never occur together. These findings raise the critical question of how the MAP kinase pathway might be activated in those tumors that do not have NRAS or BRAF mutations.

Array CGH analysis by Curtin et al., supra, found differences in the characteristics of the DNA copy number aberrations among the melanoma subtypes, with significant differences in the frequency of involvement of several loci. Examination of the copy number profiles of 103 primary melanomas from this study found gain (10 tumors) or amplification (7 tumors) of chromosome 4p12. Sixteen of these tumors had been sequenced for BRAF and NRAS and no mutations were found. All 17 tumors were of the acral, mucosal, or CSD subtypes.

The common region of 4p12 copy number elevation contains several receptor tyrosine kinases (RTK) that are attractive candidate melanoma oncogenes. These include the v-kit Hardy-Zuckerman 4 feline sarcoma viral oncogene homolog KIT, the vascular endothelial growth factor receptor KDR and platelet-derived growth factor alpha receptor (PDGFRA). KIT is an important gene for melanocyte survival and development (Chabot, et al., *Nature* 335:88-89, 1988; Geissler, et al., *Cell* 55:185-192, 1988) and subject to oncogenic mutations in a variety of cancer types (Beghini et al., *Cancer* 92:657-662, 2001; Beghini et al., *Blood Cells Molecules and Diseases* 24:262-270, 1998; Isozaki, et al., *Am. J. Path.* 157:1581-1585, 2000; Lux, et al., *Am. J. Path.* 156: 791-795, 2000; Wardelmann, et al., *Mod. Pathology* 15: 125-136, 2002). However, previous investigations have generally dismissed its importance in melanoma because expression appeared to be lost during tumor progression (Lassam & Bickford, *Oncogene* 7: 51-56, 1992; Natali, et al., *Int. J. Cancer* 52: 197-201, 1992; Zakut, et al., *Oncogene* 8: 2221-2229, 1993; Huang, et al., *Oncogene* 13: 2339-2347, 1996; Montone, et al., *Mod. Pathology* 10: 939-944, 1997). KDR is important in angiogenesis (Millauer, et al., *Cell* 72: 835-846, 1993) and in the development of solid tumors (Millauer, et al., *Nature* 367: 576-579, 1994) and is commonly expressed in melanoma (Straume & Akslen, *Am J Pathol* 159: 223-235, 2001). PDGFRA is found to be activated by mutations or small deletions in a subset of gastro-intestinal stroma tumors (GIST) (Heinrich, et al., *Science* 299: 708-710, 2003) and in childhood acute myeloid leukemia (Heinrich, et al., *Science* 299: 708-710, 2003).

Protein-tyrosine phospatases (PTPases) are a highly pleiomorphic set of molecules with roles in regulating responses of eukaryotic cells to extracellular signals by regulating the phosphotyrosine content of specific intracellular proteins. Mammalian PTPases have been divided into two broad categories: (1) transmembrane receptor PTPases which contain linked cytoplasmic catalytic domains, and (2) intracellular PTPases. Within the second category is a PTPase termed SHP2 that contains two tandem SRC homology 2 (SH2) domains located at the amino terminal end of the protein. The SH2 domains enable SHP2 to bind specific phosphotyrosine residues within protein sequences. Mutations within SHP2, most specifically within the SH2 regions of SHP2 have been associated with various disorders including: Noonan Syndrome, LEOPARD Syndrome, Juvenile Myelomonocytic Leukemia, Acute Monoblastic Leukemia and various neuroblastomas. SHP2 operates immediately downstream of KIT and cells expressing mutant SHP-2 have been shown to be sensitized to stem cell factor (SCF), the ligand for KIT, stimulation resulting in a prolonged and more intense signal of p-ERK lasting up to 60 min (Niimi, et al., *Leukemia* 20, 635-644, 2006).

The current invention is based on the discovery of certain KIT-dependent melanomas, e.g., mucosal, acral, ocular, such as conjunctival, or CSD melanomas.

BRIEF SUMMARY OF THE INVENTION

The current invention provides methods of detecting a c-Kit-dependent melanoma, e.g., a mucosal melanoma; an acral melanoma; an ocular, e.g., conjunctival, melanoma; or a CSD melanoma. The methods comprise detecting a sequence mutation and/or amplification or overexpression of c-KIT in melanoma cells from a patient. The methods can be used for diagnostic and prognostic indications and, e.g., for identifying melanoma patients that are responsive to c-Kit inhibitors. The invention also provides methods of treating melanoma comprising administering a c-Kit inhibitor to a c-Kit-dependent melanoma.

The invention additionally provide methods of detecting melanoma, e.g., mucosal, acral, ocular, e.g., conjunctival, and CSD melanomas, by detecting the presence of a mutation in SHP-2.

Thus, the invention provides a method of detecting melanoma in a biological sample, e.g., a skin sample, comprising melanoma cells from a patient having melanoma or suspected of having melanoma, the method comprising detecting a sequence mutation or an increase in copy number of c-KIT, or overexpression of c-KIT in melanoma cells present in the biological sample, wherein the presence of an activating mutation of c-KIT or the presence of an increase in c-KIT copy number is indicative of the presence of melanoma. Typically, the melanoma is acral melanoma, mucosal melanoma, CSD melanoma, or ocular, e.g., conjunctival, melanoma. In some embodiments, the detecting step comprises detecting levels of a c-KIT nucleic acid, e.g., mRNA or genomic DNA. In typical embodiments, such detection steps comprise an amplification reaction, such as PCR or RT-PCR. In other embodiments, the detecting step comprises detecting levels of c-KIT protein expression or detecting a mutation in c-KIT protein. In some embodiments, the detection step can comprise detecting multiple c-KIT defects, e.g., detecting a sequence mutation and copy number changes.

The c-KIT-dependent melanoma cells can also be detected by detecting a sequence mutation in SHP2. In some embodiment, analysis for the presence of a sequence mutation in SHP2 is performed in addition to detecting defects in c-KIT in the melanoma. The SHP2 mutation is often detected in the protein tyrosine phosphatase domain. For example, the mutation can be P491L, 1309V, or S150F in exons 13, 8, and 4, respectively. The mutation can be detected by analyzing either nucleic acids or protein. Typically, the mutation is detected by analyzing nucleic acids, e.g., either RNA or genomic DNA, from a biological sample from the patient.

Typically, the detecting step comprises detecting the presence of a sequence mutation in a c-KIT or SHP2. This is often achieved, e.g., by analyzing a nucleic acids from the biological sample. The nucleic acid can be a DNA or RNA sample. The DNA sample can be derived from reverse transcription of RNA, or can be genomic DNA. Often, the detection step for detecting the mutation comprises an amplification reaction.

In some embodiments, the melanoma is from a patient that has, or is suspected of having an acral melanoma, a mucosal melanoma, an ocular, e.g., conjunctival, or CSD melanoma.

In further embodiments, the detecting step comprises detecting the presence of a mutation in exon 11, 13, 17, or 18 of c-KIT.

In other embodiments of the invention, acral melanoma, CSD melanoma, mucosal melanoma, or ocular, e.g., conjunctival, melanoma is detected by detecting increase in copy number of the c-KIT gene and/or overexpression of the gene product. Detection methods are performed as described herein. For example, overexpression can be detected by evaluating levels of mRNA or protein. Copy number can be evaluated, e.g., by amplification methods or methods such as in situ hybridization.

The invention also provides a method of detecting the presence of melanoma cells from a melanoma that arose on the palms, soles, under the nails, from mucosal membranes, from chronically sun-exposed skin or from the eye, e.g., the uvea or conjuntiva, the method comprising detecting an increase of c-KIT copy number, or a sequence mutation in a c-KIT gene or a SHP2 gene.

In other embodiments, the presence of melanoma cells from a melanoma that rose on the palms, soles, under the nails, mucosal membranes, from chronically sun-exposed skin or ocular melanoma can be detected by detecting overexpression of c-Kit.

The invention also provides a method of monitoring progression of melanoma, e.g., in a patient subjected to a melanoma treatment regimen, in a patient having an acral, mucosal, CSD, or ocular, e.g., conjunctival or uveal, melanoma, the method comprising detecting the presence of a mutated c-KIT protein or nucleic acid; or a mutated SHP-2 protein or nucleic acid, in a biological sample from the patient.

In some embodiments, monitoring progression of melanoma in a patient having an acral, mucosal, CSD, or ocular melanoma is performed by detecting an increase in c-KIT copy number, relative to a normal control, in a biological sample from the patient; or by monitoring the number of melanoma cells that have a c-KIT or SHP2 sequence mutation in a sample suspected of comprising melanoma cells.

In other embodiments, monitoring progression of melanoma in a patient having an acral, mucosal, CSD, or ocular, e.g., conjunctival, melanoma is performed by detecting an increase in expression of c-KIT, relative to normal, in a biological sample from the patient.

Typically, in monitoring melanoma progression in accordance with the invention, the presence of a reduced number of c-KIT-dependent melanoma cells in the biological sample is indicative of a therapeutic response to the treatment agent in the patient.

In all of the detection methods of the invention the biological sample can be from any source in the body that is suspected of containing primary or metastatic melanoma cells. Thus, the biological sample can be from skin, e.g., acral skin, eye, e.g., conjunctiva, or mucosal membranes, and in other embodiments, can be from blood, serum, tissue from lymph nodes, or tissue from visceral organs. In some embodiments, for example in monitoring progression of melanoma, the sample is from a readily accessible tissue such as blood.

In another aspect, the invention provides a method of determining whether a melanoma patient is a candidate for receiving a therapy that inhibits c-Kit activity. The method comprises determining whether the melanoma that the patient has comprises melanoma cells that have an increase in c-KIT copy number and/or overexpresses c-kit and/or have a sequence mutation in c-Kit or SHP2. Detection is performed in accordance with the methods described herein. Accordingly, the detecting step can comprise detecting levels of mRNA or protein. In other embodiments, the detecting step can comprise detecting the presence of a c-kit mutation in a nucleic acid sample from the melanoma or from a protein sample from the melanoma. The nucleic acid sample can be RNA or DNA, e.g., genomic DNA or cDNA made from RNA from the melanoma sample. Often, the detecting step comprises an amplification reaction, such as PCR or RT-PCR.

In typical embodiments, the melanoma is an acral melanoma, a mucosal melanoma, an ocular melanoma, e.g., a conjunctival melanoma, or a CSD melanoma.

In another aspect, the invention provides a method of inhibiting proliferation of c-KIT-dependent melanoma cells, the method comprising administering a c-KIT inhibitor. The c-KIT inhibitor, can be, e.g., a small molecule, such as imatinib mesylate, dasatinib, sunitinib; an antibody; or a peptide. Typically, the melanoma cells are from an acral melanoma, a mucosal melanoma, an ocular, e.g., conjunctival melanoma, or a CSD melanoma.

DETAILED DESCRIPTION OF THE INVENTION

Introduction

Figure 1:
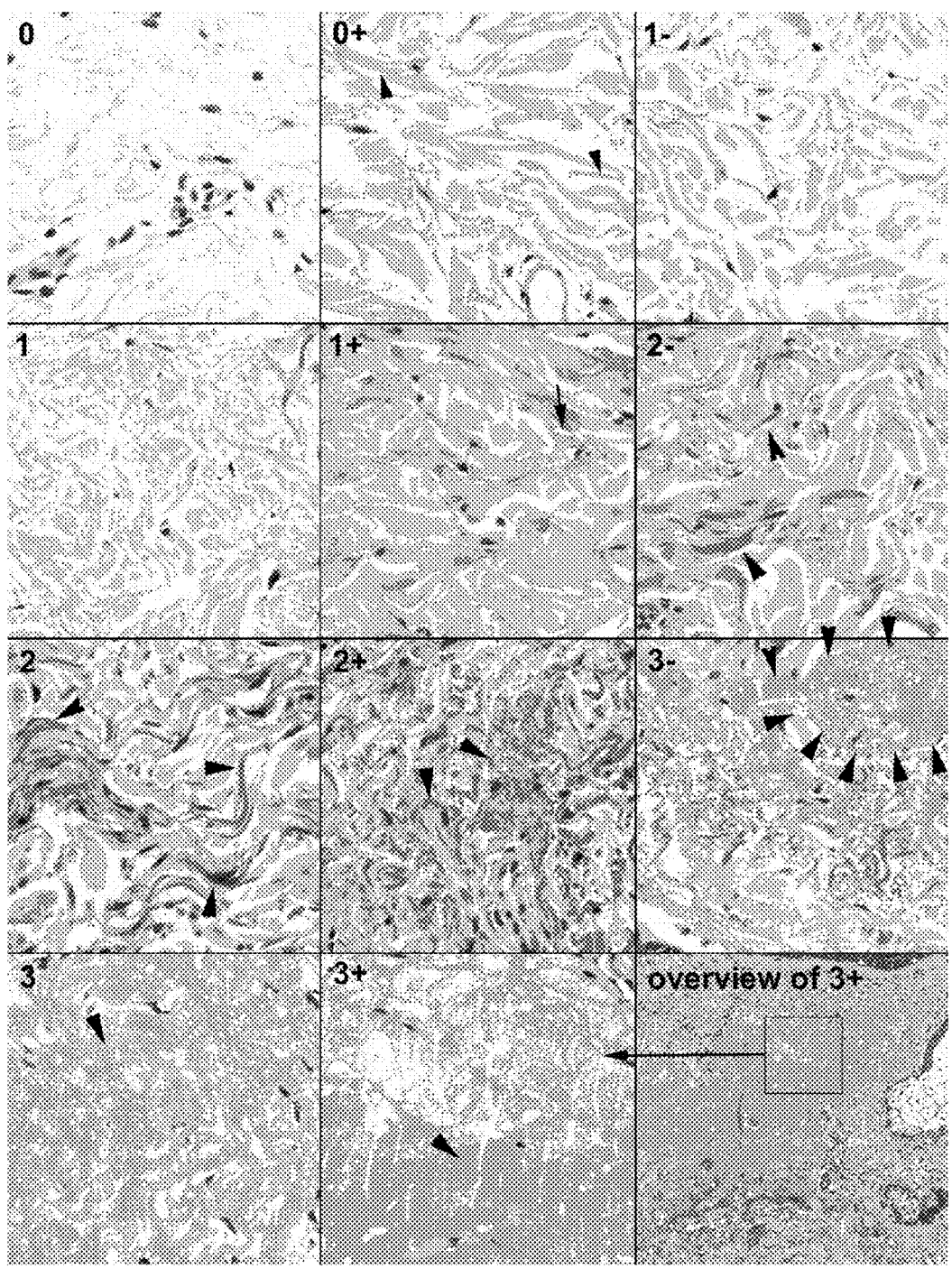
FIG. 1: panels showing representative samples of skin corresponding to chronic sun-induced damage (CSD) damage scores of CSD 0 to CSD 3.

The present invention provides methods, reagents and kits, for diagnosing cancer, for prognostic uses, and for treating melanomas. The invention is based upon the discovery that c-Kit is an oncogene in melanoma, and a therapeutic target in melanomas, e.g., melanomas of mucosal membranes, acral melanomas, melanomas from chronically sun-damaged skin, and ocular melanomas, such as conjunctival melanomas.

KIT is a 145-kd transmembrane glycoprotein that is the product of the KIT gene, the normal cellular homologue of the feline sarcoma virus oncogene v-kit. It is a member of the subclass III family of receptor tyrosine kinases and is closely related to the receptors for PDGF, M-CSF, and FLT3 ligand. The ligand for KIT, stem cell factor (SCF) promotes the dimerization and autophosphorylation of KIT receptors. The resulting phosphorylated tyrosine residues provide binding sites for signaling molecules that contain SH2 domains, including phosphatidylinositol (PI) 3-kinase. These signaling molecules activate a variety of downstream targets. KIT signaling is important for the normal development and survival of melanocytes as well as other cells. The importance of c-KIT in malignancies has been well documented (see, e.g., Heinrich et al., *J. Clin. Oncology* 20:1692-1703 for a review)

One aspect of the invention, the ability to detect melanoma cells by virtue of detecting increased c-KIT copy number, levels of expression and/or a mutant (sequence) form of c-Kit, is useful for any of a large number of applications. For example, it can be used, alone or in combination with other diagnostic methods, to diagnose melanoma, or a certain type of melanoma, in the patient. It can also be used to identify particular melanomas that are sensitive to therapeutics, such as therapeutics that target certain receptor tyrosine kinases, e.g., imatinib mesylate (mesylate is designated chemically as 4-[(4-Methyl-1-piperazinyl)methyl]-N-[4-methyl-3-[[4-(3-pyridinyl)-2-yrimidinyl]amino]-phenyl]benzamide methanesulfonate), which is a phenylaminopyrimidine tyrosine kinase inhibitor, dasatinib, and sunetinib.

The detection of c-Kit levels or the presence of mutations can also be used to monitor the efficacy of a melanoma treatment. For example, the level of a c-Kit polypeptide or polynucleotide, or the numbers of melanocytic cells that have sequence mutations in c-Kit, or an increase in copy number of a c-KIT gene, after an anti-cancer treatment can be compared to the level before the treatment. A decrease in the level of the c-Kit polypeptide or polynucleotide, or a reduction in the number of melanoma cells that have mutated c-Kit after the treatment indicates efficacious treatment. In addition, the level of c-Kit and/or presence of mutated c-Kit can be statistically correlated with the efficacy of particular anti-melanoma therapies or with observed prognostic outcomes, thereby allowing the development of databases based on which a statistically-based prognosis, or a selection of the most efficacious treatment, can be made in view of a particular level or diagnostic presence of c-Kit Detection of level of c-Kit or mutations in c-Kit, e.g., on the cell surface, can also be useful to monitor the number or location of melanoma cells in a patient, for example, to monitor the progression of the cancer over time.

SHP2 mutations have also been identified in melanoma, e.g., acral, ocular, mucosal or CSD melanomas. Accordingly, detection of SHP2 sequence mutations can also detect melanomas that are c-KIT-dependent melanomas and targets for therapy using c-KIT inhibitors.

c-KIT can also serve as a therapeutic target. Accordingly, the invention also provides methods of treating melanoma, in particular melanomas that overexpress and/or have a mutant c-KIT or mutant SHP2 by administering c-KIT inhibitors, e.g., antibodies, peptides, small molecule receptor tyrosine kinase-targeted drugs, such as imatinib mesylate or other small molecule inhibitors, and nucleic acid inhibitors of c-KIT.

Definitions

The term "c-KIT" refers to the proto-oncogene tyrosine protein kinase Kit. "c-KIT" is used interchangeably with "KIT" in this application. The term encompasses nucleic acid and polypeptide polymorphic variants, alleles, mutants, and fragments of KIT. Such sequences are well known in the art. Exemplary human KIT sequences are available under the reference sequences NM_000222 (nucleotide sequence)

in the NCBI nucleotide database and accession number P10721 (polypeptide sequence). The sequence NM_000222 is provided in SEQ ID NO:1 as an exemplary polynucleotide sequence. The exemplary polypeptide sequence P10721 is shown in SEQ ID NO:2. Human KIT shares close structural identity with KIT from other species. For example, primate KIT nucleic acid and protein sequences are over 99% similar to human KIT. Rat and mouse KIT nucleic acid and protein sequences have 80 to 85% similarly to human KIT.

The term "SHP-2" refers to the protein-tyrosine phosphatase non-receptor type 11 encoded by the ptpn11 gene which maps to the 12q24 locus. The term encompasses nucleic acid and polypeptide polymorphic variants, alleles, mutants, and fragments of SHP-2. Such sequences are well known in the art. Exemplary human SHP-2 sequences are available under the reference sequences NM_002834 (nucleotide sequence) in the NCBI nucleotide database and accession number NP_002825 (polypeptide sequence). The sequence NM_002834 is provided as SEQ ID NO:3 as an exemplary nucleotide sequence. The exemplary polypeptide sequence is shown in SEQ ID NO:4.

A "c-Kit-dependent melanoma" or "c-Kit-dependent melanoma cells" as used in the context of this application refers to a melanoma comprising melanoma cells that have a defect (also referred to as a "mutation") in c-Kit and/or a sequence mutation in SHP-2. The defect in c-Kit can be a c-Kit sequence mutation, an increase in c-Kit copy number, or overexpression of c-Kit. The "c-Kit dependent melanoma cells" may have one or more of such mutation, e.g., the melanoma cells may have a c-KIT and/or a SHP2 sequence mutation and an increase in c-Kit copy number. A "c-Kit-dependent melanoma" of the present invention typically is from acral skin, mucosa, conjunctiva, or skin with signs of chronic sun-induced damage.

In the context of this application "acral melanoma" refers to melanoma occurring on the non-hair-bearing skin of the palms or soles or under the nails. A subset of acral melanomas are "acral-lentiginous melanomas"

The term "mucosal melanoma" refers to tumors arising on mucosal membranes; "ocular melanoma" as used herein is melanoma that arises from the eye. "Ocular melanoma" includes uveal and conjunctival melanoma. "Conjunctival melanoma" refers to a melanoma that arises on the conjunctiva.

"CSD melanoma" as used herein refers to melanoma arising from skin with chronic sun-induced damage; and "NCSD melanoma" as used herein refers to melanoma arising from skin without chronic sun-induced damage. The distinction between the "CSD" and "NCSD" groups in the instant application is based on the presence or absence on microscopy of marked solar elastosis of the dermis surrounding the melanomas. In all but a few cases, melanomas associated with chronic sun-induced damage (CSD) occur on the face and distal extremities such as the forearms, dorsal hands, shins and calfs. These melanomas typically occur in individuals older than 50 years of age, and microscopically, have an intraepidermal component in which melanocytes are arranged as solitary units rather than nests. In addition, these melanomas tend to have an atrophic epidermis with the effacement of the rete ridges. A subset of the CSD melanomas is lentigo maligna melanomas. By contrast melanomas that were not associated with chronic sun-induced damage (NCSD) occur on the trunk and proximal extremities such as thighs and upper arms. The NCSD melanomas typically show an intraepidermal component in which melanocytes are arranged as nests rather than solitary units and display considerable upward scatter (pagetoid spread). Many of the NCSD melanomas are superficial spreading melanomas.

Chronic sun-induced damage is defined as having a CSD score greater than CSD 2. The scores are obtained by determining the degree of solar elastosis on hematoxylin-and-eosin (H&E) stained sections of normal skin surrounding the melanomas at 100-200× magnification using the following system (Landi et al., *Science* 2006), examples of which are provided in FIG. 1:

CSD 0: absence of elastotic fibers; CSD 0+: rare elastotic fibers discernible only at 200× magnification;

CSD 1: scattered elastotic fibers lying as individual units, not as bushels, between collagen bundles; "−" or "+" classifiers were used to indicate whether the elastotic fibers were scarcely or densely scattered.

CSD 2: densely scattered elastotic fibers distributed predominantly as bushels rather than individual units; The "−" classifier was used to indicate that bushels were present, but elastotic fibers distributed as individual units predominated; The "+" classifier was used when larger aggregates of bushels formed, but preserving the outline of individual bushels instead of forming amorphous deposits;

CSD 3: amorphous deposits of blue-gray material with lost fiber texture; "−" only focal formation of amorphous deposits; "+" very large agglomerates of diffuse basophilic material.

All images in FIG. 1 were taken with the 40× objective except for the lower right, which shows an overview with the 10× objective.

As used herein, the term "determining that the melanoma arose from" a site, e.g., acral skin, mucosa, conjunctiva, or skin having chronic sun-induced damage, refers to identifying the site of origin of a melanoma. Such a determination can be performed by visual inspection of a patient or by a pathology evaluation of the melanoma.

The terms "tumor" or "cancer" in an animal refers to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumor, but such cells may exist alone within an animal. "Tumor" includes both benign and malignant neoplasms. The term "neoplastic" refers to both benign and malignant atypical growth.

"Biological sample" as used herein refers to a sample obtained from a patient suspected of having, or having, melanoma. In some embodiments, the sample may be a tissue biopsy, which refers to any type of biopsy, such as needle biopsy, fine needle biopsy, surgical biopsy, etc. The sample typically comprises a skin tissue sample harboring the lesion or suspected lesion, although the biological sample may be also be derived from another, site, e.g., a site to which a melanoma may metastasize, or from the blood. In some cases, the biological sample may also be from a region adjacent to the lesion or suspected lesion.

"Providing a biological sample" means to obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, can also be used.

A patient that is "a candidate for receiving a receptor tyrosine kinase-based therapy" refers to a patient that has a melanoma that has a defect in c-KIT, such that c-KIT is increased in copy number, overexpressed and/or has a sequence mutation; or a patient that has a sequence mutation, either alone or in combination with a c-KIT defect, in SHP-2, e.g., in the protein tyrosine phosphatase domain of SHP-2.

A "receptor tyrosine kinase-based therapy" refers to an agent that inhibits c-KIT, including small molecule agents such as imatinib mesylate, dasatinib, or sunitinib, or analogs thereof, antibodies, and the like.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). For the purposes of this invention, BLAST and BLAST 2.0 are used with default parameters to determine percent sequence identity for the nucleic acids and proteins of the invention. Software for performing BLAST analyses is publicly available through the National Center for Biotechnology Information (NCBI). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid (protein) sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915)). For the purposes of this invention, the BLAST2.0 algorithm is used with the default parameters and the filter off.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., *Tetrahedron* 49(10):1925 (1993) and references therein;

Letsinger, J. Org. Chem. 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., *Chem. Int. Ed. Engl.* 31:1008 (1992); Nielsen, Nature, 365:566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995); non-ionic backbones (U.S. Pat. Nos. 5,386,023, 5,637,684, 5,602,240, 5,216,141 and 4,469,863; Kiedrowski et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., *Chem. Soc. Rev.* (1995) pp 169-176). Several nucleic acid analogs are described in Rawls, C & E News Jun. 2, 1997 page 35. All of these references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched base-pairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses conservatively modified variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the KIT nucleic acids, proteins and antibodies at any position. Any method known in the art for conjugating the antibody to the label may be employed, e.g., using methods described in Hermanson, *Bioconjugate Techniques* 1996, Academic Press, Inc., San Diego.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. Similarly, a "recombinant protein" is a protein made using recombinant techniques, i.e., through the expression of a recombinant nucleic acid as depicted above.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

The phrase "functional effects" in the context of assays for testing compounds that inhibit activity of a c-KIT protein includes the determination of a parameter that is indirectly or directly under the influence of the c-KIT cancer protein or nucleic acid, e.g., a functional, physical, or chemical effect, such as the ability to decrease tumorigenesis. Activities or functional effect of c-KIT include protein-protein interaction activity, e.g., the ability of c-KIT to bind an antibody or other protein with which it interacts; receptor tyrosine kinase activity, the ability of c-KIT to bind a ligand, cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo, including measurement of tumor growth and tumor "take" in a model system; mRNA and protein expression in cells, including those undergoing metastasis, and other characteristics of cancer cells. "Functional effects" include in vitro, in vivo, and ex vivo activities.

"Inhibitors" of c-KIT refer to inhibitory molecules or compounds that, e.g., bind to, partially or totally block activity, decrease, prevent, delay activation, inactivate, desensitize, or down regulate the activity or expression of c-KIT proteins, e.g., antagonists. Inhibitors include siRNA or antisense RNA, genetically modified versions of c-KIT proteins, e.g., versions with altered activity, as well as naturally occurring and synthetic KIT antagonists, antibodies, small chemical molecules and the like. Inhibitors are known, further assays for identifying inhibitors can be performed in vitro or in vivo, e.g., in cells, or cell membranes, by applying test inhibitor compounds, and then determining the functional effects on activity, Samples or assays comprising c-KIT proteins that are treated with a potential inhibitor are compared to control samples without the inhibitor, to examine the extent of inhibition. Control samples (untreated with inhibitors) are assigned a relative protein activity value of 100% Inhibition of c-KIT is achieved when the activity value relative to the control is about 80%, preferably 50%, more preferably 25-0%.

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique pp.* 231-241 ($3^{rd}$ ed. 1994).

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol*:5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., *Nature* 321:522-525 (1986); Riechmann et al., *Nature* 332:323-329 (1988); and Presta, *Curr. Op. Struct. Biol.* 2:593-596 (1992)). Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

The term "fully human antibody" refers to an immunoglobulin comprising human variable regions in addition to human framework and constant regions. Such antibodies can be produced using various techniques known in the art. For example in vitro methods involve use of recombinant libraries of human antibody fragments displayed on bacteriophage (e.g., McCafferty et al., 1990, *Nature* 348:552-554; Hoogenboom & Winter, J. Mol. Biol. 227:381 (1991); and Marks et al., *J. Mol. Biol.* 222:581 (1991)), yeast cells (Boder and Wittrup, 1997, *Nat Biotechnol* 15:553-557), or ribosomes (Hanes and Pluckthun, 1997, *Proc Natl Acad Sci USA* 94:4937-4942). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584, 5,545,807; 5,545,806; 5,569,825; 5,625,126; 5,633,425; 5,661,016, and in the following scientific publications: (e.g., Jakobavits, *Adv Drug Deliv Rev.* 31:33-42 (1998), Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); Lonberg & Huszar, *Intern. Rev. Immunol.* 13:65-93 (1995).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

General Recombinant Methods

This invention relies on routine techniques in the field of recombinant genetics for the preparation of c-Kit for use in the invention and for methods of detecting c-Kit. Basic texts disclosing the general methods of use in this invention include Sambrook & Russell, Molecular Cloning, A Laboratory Manual (3rd Ed, 2001); Kriegler, Gene Transfer and Expression: A Laboratory Manual (1990); and Current Protocols in Molecular Biology (Ausubel et al., eds., 1994-1999). For example, in applications in which c-KIT, or a fragment of c-KIT is to be produced, e.g., for use in an assay to detect inhibitors, routine expression protocols are employed.

Identification of c-Kit or SHP2 Sequences in a Sample from a Patient

In one aspect of the invention, the presence of increased levels of c-KIT polynucleotide, e.g., mRNA, or increased levels of c-KIT protein and/or the presence of sequence mutations in c-KIT or SHP2 is determined in biological samples suspected of comprising melanoma cells.

In some embodiments mutations in c-KIT are determined. As noted, human KIT sequences are well known. In addition to the mRNA and protein sequences (exemplary accession numbers, supra). The genomic sequence is known (see, e.g., Vandenbark, *Oncogene* 1992 July; 7(7):1259-66). Polymorphic variants are also known that do not influence activity, including single nucleotide polymorphisms in intron, untranslated regions, and in the coding sequence that result in no change in amino acid sequence or in a conservative change (see, e.g., the NCBI SNP database). The gene spans 89 kb and has 21 exons. The mRNA transcript is 5.23 kb. Alternative splicing of exon 9 gives rise to two isoforms, KitA and Kit, that differ by the presence or absence of four amino acids.

"Sequence mutation" as used in this application refers to changes in a polynucleotide sequence that result in changes to protein activity. Mutations can be nucleotide substitutions, such as single nucleotide substitutions, insertions, or deletions. C-kit mutations detected in acral, mucosal, CSD, or ocular melanoma in the current invention are typically activating mutations that lead to activation of c-kit activity.

The full-length KIT protein is 976 amino acids in length and contains various domains characteristic of this family of growth factor receptors, including 5 immunoglobulin-like C2-type domains in the extracellular region, three of which are involved in ligand binding. The binding of ligand to c-KIT leads to its homodimerization and activation of its intrinsic intracellular tyrosine kinase enzymatic activity, with subsequent autophosphorylation. The intracellular region of c-Kit contains two tyrosine kinase domains, TK I and TK II, as well as a juxtamembrane domain that negatively regulates the TK I and TK II domains. The structure of the active c-kit kinase has been determined (see, e.g., Mol et al., *J Biol Chem* 2003 Aug. 22; 278(34):31461-64). Loss of function and gain of function mutations are known.

Various gain-of-function mutations have been identified in malignancies, which result in SCF-independent, constitutive activation of c-Kit. The tyrosine kinase activity of KIT can be activated by mutations of several different exons of the c-kit gene (see, e.g., the review by Heinrich et al., supra). Exons 1-9 encompass the extracellular domains and exons 11-17 encode the intracellular domains. Exon 10 encodes the transmembrane domain, exon 11 encodes the intracellular juxtamembrane domain, and exons 13 and 17 are the tyrosine kinase domains. Mutations in exon 2 of the extracellular portion have been described in myeloproliferative disorders, mutations in exon 8 have been identified in acute myeloid leukemia, and in exon 9 in gastrointestinal stromal tumors. Mutations in exon 11, which is the juxtamembrane domain of c-Kit that negatively regulates the tyrosine kinase domains of exons 13 and 17, have been described in human gastrointestinal stromal tumors. This is the most common site of mutation in human gastrointestinal stromal tumors. Mutations in exons 13 and 17, which code for the tyrosine kinase domains of c-Kit, are detected frequently in systemic mastocytosis, core factor binding leukemias, and seminomas. Mutations in the tyrosine kinase domains affect the ATP binding ability of c-Kit, and can yield gain-of-function or loss-of-function tyrosine kinase activity. Mutations in the c-Kit juxtamembrane region cluster around the two main autophosphorylation sites that mediate PTB binding, Tyr-568 and Tyr-570, and are associated with human gastrointestinal stromal tumors. Mutations in the kinase domain are found in mast cell and myeloid leukemias and in human germ cell tumors.

The current invention is based on the discovery of mutations in common c-KIT mutations sites in melanoma, for example in mucosal, acral, and CDS melanomas. A mutation may be in any part of the c-KIT gene. Common sequence mutations sites are present in exons 11, 13, 17 and 18. Exemplary mutations that can be identified in the current invention are shown in Table 3. These mutations include the following mutations: K642E, L576P, D816H, V559A, A829P, and intronic deletion, R634W, Y553N, and N566d. As noted in Table 3, some of these mutations have not been previously reported. As understood in the art, the particular mutation is commonly referred to by the change in amino acid sequence that results from the mutation in the nucleic acid sequence.

In the present invention overexpression and/or sequence mutation in C-KIT are detected for the diagnosis (or for prognostic indications) of melanoma, e.g., for the diagnosis of subtypes of melanoma such as acral, mucosal, CDS, and ocular melanomas. Thus, biological samples obtained from patients that have or are suspected of having melanoma can be analyzed for increases in C-KIT copy number, overexpression of C-KIT mRNA, overexpression of C-KIT protein, and for the presence of mutations in C-KIT. The presence of mutations is conveniently analyzed by analyzing nucleic acid samples, either RNA or DNA, from the biological sample, but may also be determined by analyzing protein.

SHP2 Sequence Mutations

SHP2 (also known as PTPN11) encodes the non receptor-type protein tyrosine phosphatase, Src homology region 2-domain phosphatase-2 (SHP-2) and functions as an intracellular signal transducer that associates with tyrosine kinase receptors, and scaffolding adapters (Tartaglia & Gelb, *Ann. Rev. Genom. and Hum. Gen.* 6:45-68, 2005). Nucleic acid and protein from melanoma cells, e.g., melanoma cells from acral, mucosal, ocular, or CSD melanomas, from a patient can also be evaluated for the presence of SHP2 sequence mutations. Typically, the method comprises detecting a mutation in the protein tyrosine phosphatase domain, e.g., a P491L, a S150F, or a I309V substitution. Detection of the mutant sequence is typically performed by evaluating nucleic acid samples from melanoma cells from the patient. The evaluation can be performed using methods well known in the art, including, for example, sequence analysis, use of allele-specific oligonucleotides, and the like. The methods employed are the same as those used to determine sequence mutations in c-Kit.

Mutations in SHP2 can also be determined by evaluating protein samples, e.g., using specific antibodies.

Detection of Copy Number

In one embodiment, diagnostic and prognostic detection of c-Kit in cancer is performed by determining the copy number of c-Kit, i.e., the number of DNA sequences in a cell encoding c-Kit. Methods of evaluating the copy number of a particular gene are well known to those of skill in the art, and include, inter alia, hybridization and amplification based assays. An increase in c-KIT copy number in the instant invention is determined using a probe that selectively hybridizes to c-KIT.

In some embodiments, c-Kit copy number in a sample is determined by in situ hybridization, e.g., fluorescence in situ hybridization, or FISH. In situ hybridization assays are well known (e.g., Angerer (1987) Meth. Enzymol 152: 649). The probes used in such applications specifically hybridize to c-KIT. The probes are labeled, typically with fluorescent labels. Preferred probes are sufficiently long, e.g., from about 50, 100, or 200 nucleotides to about 1000 or more nucleotides, so as to specifically hybridize with the target nucleic acid(s) under stringent conditions.

Any of a number of other hybridization-based assays can be used to detect the copy number of c-Kit in the cells of a biological sample. For example, dot blots, array-based assays and the like can be used to determine c-Kit copy number.

In other embodiment, amplification-based assays are used to measure the copy number of c-Kit and can to determine levels of c-Kit transcripts. In such an assay, the c-Kit nucleic acid sequences act as a template in an amplification reaction (e.g., Polymerase Chain Reaction, or PCR). Such amplifications reactions are performed quantitatively. In a quantitative amplification, the amount of amplification product will be proportional to the amount of template in the original sample. Comparison to appropriate controls provides a measure of the copy number or level of RNA transcript. Methods of quantitative amplification are well known to those of skill in the art. Detailed protocols for quantitative PCR of DNA and RNA samples are known (see, e.g., Innis et al. (1990) PCR Protocols, A Guide to Methods and Applications, Academic Press, Inc. N.Y.). The known nucleic acid sequences for c-KIT (see, e.g., SEQ ID NO:1) is sufficient to enable one of skill to routinely select primers to amplify any portion of the gene. Suitable primers for amplification of specific sequences can be designed using principles well known in the art (see, e.g., Dieffenfach & Dveksler, PCR Primer: A Laboratory Manual (1995)).

Other suitable amplification methods include, but are not limited to, ligase chain reaction (LCR) (see, Wu and Wallace (1989) Genomics 4: 560, Landegren et al. (1988) Science 241: 1077, and Barringer et al. (1990) Gene 89: 117), transcription amplification (Kwoh et al. (1989) Proc. Natl. Acad. Sci. USA 86: 1173), self-sustained sequence replication (Guatelli et al. (1990) Proc. Nat. Acad. Sci. USA 87: 1874), dot PCR, and linker adapter PCR, etc.

The presence of mutations in c-KIT DNA or RNA sequences can be determined using any technique known in the art. For example, in one embodiment, allele-specific oligonucleotide hybridization may be used, which relies on distinguishing a mutant from a normal nucleic acid sequence using an oligonucleotide that specifically hybridizes to the mutant or normal nucleic acid sequence. This method typically employs short oligonucleotides, e.g., 15-20 nucleotides, in length, that are designed to differentially hybridize to the normal or mutant allele. Guidance for designing such probes is available in the art. The presence of a mutant allele is determined by determine the amount of allele-specific oligonucleotide that hybridizes to the sample Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099.

Allele-Specific Primers

In other embodiments, the presence (or amount) of a normal or mutant c-KIT nucleic acid can be detected using allele-specific amplification or primer extension methods. These reactions typically involve use of primers that are designed to specifically target a normal or mutant allele via a mismatch at the 3' end of a primer. The presence of a mismatch effects the ability of a polymerase to extend a primer when the polymerase lacks error-correcting activity. The amount of amplified product can be determined using a probe or by directly measuring the amount of DNA present in the reaction.

Detection of increased levels of c-KIT nucleic acids or the presence of a c-KIT mutation can also be performed using a 5'-nuclease activity (also referred to as a "TaqMan®" assay), e.g., as described in U.S. Pat. Nos. 5,210,015; 5,487,972; and 5,804,375; and Holland et al., 1988, Proc. Natl. Acad. Sci. USA 88:7276-7280. In such an assay, labeled detection probes that hybridize within the amplified region are added during the amplification reaction. In some embodiments, the hybridization probe can be an allele-specific probe that discriminates a normal or mutant allele. Alternatively, the method can be performed using an allele-specific primer and a labeled probe that binds to amplified product. In other embodiments, the probe may not discriminate between a mutant and normal allele.

In other embodiments, the presence of a mutant c-KIT allele can be convenient determined using DNA sequencing, such as pyrosequenceing, or other known sequencing techniques. Other detection methods include single-stranded conformational polymorphism detection methods and denaturing gradient gel electrophoresis analysis.

As indicated above, in some embodiments, levels of c-KIT RNA are detected. Methods of detecting and/or quantifying the level of c-Kit gene transcripts (mRNA or cDNA made therefrom) using nucleic acid hybridization techniques are known to those of skill in the art. For example, expression levels of c-Kit can also be analyzed by techniques such as dot blotting, in situ hybridization, RNase protection, probing DNA microchip arrays, and the like.

The level of c-KIT transcripts or the presence of a mutation in the transcript can also be detected amplification-based methods (e.g., RT-PCR). RT-PCR methods are well known to those of skill (see, e.g., Ausubel et al., supra). Preferably, quantitative RT-PCR, e.g., a TaqMan® assay, is used, thereby allowing the comparison of the level of mRNA in a sample with a control sample or value.

Detection of c-Kit Polypeptide Sequences

Altered c-Kit expression or activity can also be detected by detecting levels of c-Kit protein or activity. For example, detection of c-Kit protein activity or expression can be used for diagnostic purposes or in screening assays. In some embodiments, c-Kit level is conveniently determined using immunological assays to detect the level of c-Kit polypeptides. The following section discusses immunological detection of c-Kit. The section also relates to generation and engineering of antibodies that can be used, e.g., in therapeutic applications.

Immunological Detection c-Kit

Antibodies can be used to detect c-Kit or can be assessed in the methods of the invention for the ability to inhibit c-Kit. c-Kit can be detected and/or quantified using any of a number of well recognized immunological binding assays. A general overview of the applicable technology can be found in Harlow & Lane, Antibodies: A Laboratory Manual (1988) and Harlow & Lane, Using Antibodies (1999). Other resources include see also Methods in Cell Biology: Antibodies in Cell Biology, volume 37 (Asai, ed. 1993); Basic and Clinical Immunology (Stites & Terr, eds., 7th ed. 1991, and Current Protocols in Immunology (Coligan, et al. Eds, John C. Wiley, 1999-present) Immunological binding assays can use either polyclonal or monoclonal antibodies. In some embodiments, antibodies that specifically detect mutant c-KIT molecules may be employed.

Commonly used assays include noncompetitive assays, e.g., sandwich assays, and competitive assays. In competitive assays, the amount of c-Kit present in the sample is measured indirectly by measuring the amount of a known, added (exogenous) c-Kit displaced (competed away) from an anti-c-Kit antibody by the unknown c-Kit present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers, which are then detected according to standard techniques (see Monroe et al., Amer. Clin. Prod. Rev. 5:34-41 (1986)).

Immunoassays also often use a labeling agent to specifically bind to and label the complex formed by the antibody and antigen. The labeling agent may itself be one of the moieties comprising the antibody/antigen complex. Thus, the labeling agent may be a labeled c-Kit polypeptide or a labeled anti-c-Kit antibody. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. The labeling agent can be modified with a detectable moiety, such as biotin, to which another molecule can specifically bind, such as streptavidin. A variety of detectable moieties are well known to those skilled in the art.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent compounds (e.g., fluorescein isothiocyanate, Texas red, rhodamine, fluorescein, and the like), radiolabels, enzymes (e.g., horse radish peroxidase, alkaline phosphatase and others commonly used in an ELISA), streptavidin/biotin, and colorimetric labels such as colloidal gold or colored glass or plastic beads (e.g., polystyrene, polypropylene, latex, etc.). Chemiluminescent compounds may also be used. For a review of various labeling or signal producing systems that may be used, see U.S. Pat. No. 4,391,904.

Antibodies to c-Kit are commercially available. In some embodiments, mutations to c-Kit can be detected using antibodies that specifically bind a mutant form, thus immunoassays can also be used to detect mutant c-Kit proteins.

c-Kit or a fragment thereof, e.g., the extracellular domain, or the juxtaposition domain, may be used to produce antibodies specifically reactive with c-Kit. For example, a recombinant c-Kit or an antigenic fragment thereof, is isolated. Recombinant protein is the preferred immunogen for the production of monoclonal or polyclonal antibodies. Alternatively, a synthetic peptide derived from the sequences disclosed herein and conjugated to a carrier protein can be used as an immunogen. Naturally occurring protein may also be used either in pure or impure form. The product is then used to generate antibodies.

Methods of producing polyclonal and monoclonal antibodies that react specifically with c-KIT are known to those of skill in the art (see, e.g., Coligan; Harlow & Lane, both supra). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)). Such antibodies can be used for diagnostic or prognostic applications, e.g., in the detection of melanomas or for other cancers that exhibit increased expression or activity of c-Kit.

Typically, polyclonal antisera with a titer of 104 or greater are selected and tested for their cross reactivity against non-c-Kit proteins or even other related proteins from other organisms, using a competitive binding immunoassay. Specific polyclonal antisera and monoclonal antibodies will usually bind with a Kd of at least about 0.1 mM, more usually at least about 1 µM, optionally at least about 0.1 µM or better, and optionally 0.01 µM or better.

In some embodiments, a c-Kit antibody may be used for therapeutic applications. For example, in some embodiments, such an antibody may used to reduce or eliminate a biological function of c-Kit as is described below. That is, the addition of anti-c-Kit antibodies (either polyclonal or preferably monoclonal) to malignant melanoma tissue (or a cell population containing cancerous cells) may reduce or eliminate the melanoma. Generally, at least a 25% decrease in activity, growth, size or the like is preferred, with at least about 50% being particularly preferred and about a 95-100% decrease being especially preferred.

Often, the antibodies to the c-Kit proteins for therapeutic applications are humanized antibodies (e.g., Xenerex Biosciences, Mederex, Inc., Abgenix, Inc., Protein Design Labs, Inc.) Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332:323-329 (1988); and Presta, Curr. Op. Struct. Biol. 2:593-596 (1992)). Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

Human antibodies can also be produced using various techniques known in the art, including phage display libraries (Hoogenboom & Winter, J. Mol. Biol. 227:381 (1991); Marks et al., J. Mol. Biol. 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., J. Immunol. 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al., Nature 368: 856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

Detection of Activity

As appreciated by one of skill in the art, c-Kit activity can be detected to evaluate expression levels or for identifying inhibitors of activity. The activity can be assessed using a variety of in vitro and in vivo assays, including ligand binding activity and tyrosine kinase activity. In some embodiments, discussed in greater detail below, inhibitors can be identified using additional endpoints, such as those associated with transformation. Typically c-Kit activity is determined by measuring the ability to bind a protein to which it interacts, e.g., an antibody, ligand, or other protein, such as signaling molecules that contain SH2 domains Disease Diagnosis/Prognosis c-Kit and SHP2 nucleic acid and polypeptide sequences can be used for diagnosis or prognosis of melanoma in a patient. For example, as described above, the sequence, level, or activity of c-Kit in a melanoma sample from a patient can be determined, wherein an alteration, e.g., an increase in the level of expression or activity of c-Kit, or the detection of an increase in copy number or a sequence mutation in c-Kit, indicates the presence or the likelihood of melanoma.

Often, such methods will be used in conjunction with additional diagnostic methods, e.g., detection of other melanoma indicators, e.g., cell morphology, and the like. In other embodiments, a tissue sample known to contain melanoma cells, e.g., from a tumor, will be analyzed for c-Kit defects to determine information about the cancer, e.g., the efficacy of certain treatments, such as therapeutics that target receptor tyrosine kinases, such as imatinib mesylate, the survival expectancy and the like.

In some embodiments, analysis of melanoma cells for the presence of c-Kit defects or a SHP2 sequence mutation can be used to determine the prognosis of a patient with melanoma or for determining progression of the disease. For example, if melanoma is detected using a technique other than by detecting c-Kit, e.g., tissue biopsy, then the presence or absence of a c-Kit defect can be used to determine the prognosis for the patient, i.e., the presence of a defect in c-Kit, or SHP2 sequence mutation, will typically indicate a reduced survival expectancy in the patient compared to in a patient with melanoma but with a normal level of c-Kit. As used herein, "survival expectancy" refers to a prediction regarding the severity, duration, or progress of a disease, condition, or any symptom thereof. A "diagnostic presence" can be an increase in c-KIT copy number, increased levels of c-KIT mRNA or protein and/or the presence of sequence mutations in c-KIT or SHP2 that alter function.

Any biological sample suspected of containing melanoma cells can be evaluated to determine progression. For example, tissues from visceral organs, blood, lymph nodes and the like can be analyzed for the presence of C-KIT or SHP2 sequence mutations and/or increases in C-KIT copy number and/or expression.

The presence of a particular mutation may also indicate that a melanoma may or may not be responsive to certain treatments, e.g., imatinib mesylate. For example, melanomas having mutations in the juxtamembrane region may not be responsive to imatinib mesylate.

The methods of the present invention can be used to determine the optimal course of treatment in a patient with cancer. For example, the presence of an increase in c-KIT copy number and/or an elevated level of c-Kit and/or a sequence mutation in c-Kit can indicate that certain therapeutics, such as those that target receptor tyrosine kinases, will be beneficial to those patients. In addition, a correlation can be readily established between the presence of a defect in c-Kit and/or a sequence mutation in SHP2, and the relative efficacy of one or another anti-melanoma agent. Such analyses can be performed, e.g., retrospectively, i.e., by analyzing for a c-Kit defect and/SHP2 sequence mutation in samples taken previously from patients that have subsequently undergone one or more types of anti-cancer therapy, e.g., therapies that target receptor tyrosine kinases, and correlating the presence of the defect with the known efficacy of the treatment.

Screening for Inhibitors or Modulators of c-KIT

In another aspect, this invention includes methods of treating melanoma that overexpress and/or have a mutation in c-KIT where the method comprises administering an inhibitor of c-KIT. Inhibitors of c-KIT are known, including, e.g., imatinib mesylate. Imatinib mesylate, which inhibits the oncoprotein product of the Philadelphia chromosome translocation, BCR-ABL, inhibits other members of the split tyrosine kinase domain type III receptor family, including Kit, PDGF-Rα and FLT-3 (see, e.g., the review by Wong & Witte in *Annu Rev Immunol*. 22:247-306, 2004). Other small molecule inhibitors of KIT tyrosine kinase activity have also been identified. These include indolinones and anilinophthalazines (see, e.g., Ma et al., *J. Invest. Dermatol*. 114:392-394, 2000; Smolich et al. *Blood* 97:1413-1421, 2001; Krystal et al. *Cancer Res*. 61:3660-3668, 2001; Mendel et al., *Anticancer Drug Des* 15:29-41, 2000; and Wood et al. *Cancer Res*. 60:2178-2189, 2000). Particular drugs in these classes include SU6668 and SU5416 (Sugen Inc. South San Francisco, Calif.).

Other inhibitors include inhibitors such as antibodies, peptide, nucleic acids and the like. As used herein, a c-Kit inhibitor is a molecule that modulates c-Kit nucleic acid expression and/or c-Kit protein activity.

Method of screening for modulators of compounds can employ, for example, melanoma cells in which c-kit is over-expressed or amplified. Such modulators may be candidate receptor tyrosine kinase modulators.

Additional c-kit inhibitors can be identified by assaying for c-kit activity, e.g., binding or enzymatic activity. Such assays employ known c-kit sequences or fragments, e.g, the extracellular domain of c-kit, or variants thereof. An exemplary human c-kit sequence polypeptide sequence that could be used in such assays is provided in SEQ ID NO:2.

Activity assays are used to identify inhibitors that can be used as therapeutic agents, e.g., antibodies to c-Kit and antagonists of c-Kit activity Inhibitors of c-Kit activity are tested using c-Kit polypeptides, either recombinant or naturally occurring. The protein can be isolated, expressed in a cell, expressed in tissue or in an animal, either recombinant or naturally occurring. For example, transformed cells can be used. Modulation is tested using one of the in vitro or in vivo assays described herein. Activity can also be examined in vitro with soluble or solid state reactions, using a c-Kit fragment that binds to another protein, e.g, a c-KIT ligand.

In another embodiment, mRNA and/or protein expression levels can be measured to assess the effects of a test compound on c-Kit expression levels. A host cell expressing c-Kit is contacted with a test compound for a sufficient time to effect any interactions, and then the level of mRNA or protein is measured. The amount of time to effect such interactions may be empirically determined, such as by running a time course and measuring the level of expression as a function of time. The amount of expression may be measured by using any method known to those of skill in the art to be suitable.

The amount of expression is then compared to the amount of expression in the absence of the test compound. A substantially identical cell may be derived from the same cells from which the recombinant cell was prepared but which had not been modified by introduction of heterologous DNA. A difference in the amount of expression indicates that the test compound has in some manner altered c-Kit levels.

In assays to identify c-Kit inhibitors, samples that are treated with a potential inhibitor are compared to control samples to determine the extent of modulation. Control samples (untreated with candidate inhibitors) are assigned a relative activity value of 100. Inhibition of c-Kit is achieved when the activity value relative to the control is about 80%, optionally 50%, optionally 25-0%.

The compounds tested as inhibitors of c-Kit can be any small chemical compound, or a biological entity, e.g., a macromolecule such as a protein, sugar, nucleic acid or lipid. Alternatively, modulators can be genetically altered versions of c-Kit. Typically, test compounds will be small chemical molecules and peptides or antibodies.

In some embodiments, the agents have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5H-bond donors (expressed as the sum of OHs and NHs); having a molecular weight over 500; having a Log P over 5 (or MLog P over 4.15); and/or having more than 10H-bond acceptors (expressed as the sum of Ns and Os). See, e.g., Lipinski et al. *Adv Drug Delivery Res* 23:3-25 (1997). Compound classes that are substrates for biological transporters are typically exceptions to the rule.

Essentially any chemical compound can be used as a potential modulator or ligand in the assays of the invention. Most often, compounds can be dissolved in aqueous or organic (especially DMSO-based) solutions. The assays are designed to screen large chemical libraries by automating the assay steps, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

Expression Assays

Certain screening methods involve screening for a compound that modulates the expression of c-Kit. Such methods generally involve conducting cell-based assays in which test compounds are contacted with one or more cells expressing a c-Kit and then detecting a decrease in expression (either transcript or translation product). Such assays are often performed with cells that overexpress c-Kit.

Expression can be detected in a number of different ways. As described herein, the expression levels of the protein in a cell can be determined by probing the mRNA expressed in a cell with a probe that specifically hybridizes with a c-Kit transcript (or complementary nucleic acid derived therefrom). Alternatively, protein can be detected using immunological methods in which a cell lysate is probed with antibodies that specifically bind to the protein.

Other cell-based assays are reporter assays conducted with cells that do not express the protein. Often, these assays are conducted with a heterologous nucleic acid construct that includes a promoter that is operably linked to a reporter gene that encodes a detectable product.

Nucleic Acid Inhibitors

In some embodiments, c-KIT inhibitors are nucleic acid molecules. For example, ribozymes, antisense RNA and/or small interfering RNA (siRNA) molecules can be used to target c-Kit.

In some embodiments, siRNA molecules are used as c-KIT inhibitors. In mammalian cells, introduction of long dsRNA (>30 nt) often initiates a potent antiviral response, exemplified by nonspecific inhibition of protein synthesis and RNA degradation. The phenomenon of RNA interference is described and discussed, e.g., in Bass, *Nature* 411:428-29 (2001); Elbahir et al., *Nature* 411:494-98 (2001); and Fire et al., *Nature* 391:806-11 (1998), where methods of making interfering RNA also are discussed. The siRNAs based upon the c-Kit sequences disclosed herein are less than 100 base pairs, typically 30 bps or shorter, and are made by approaches known in the art. Exemplary siRNAs according to the invention could have up to 29 bps, 25 bps, 22 bps, 21 bps, 20 bps, 15 bps, 10 bps, 5 bps or any integer thereabout or therebetween.

The siRNA can comprise two complementary molecules, or can be constructed such that a single transcript has both the sense and complementary antisense sequences from the target gene, e.g., a hairpin.

Methods for designing double stranded RNA to inhibit gene expression in a target cell are known (see, e.g., U.S. Pat. No. 6,506,559; Elbashir et al. *Methods* 26:199-213, 2002; Chalk et al., *Biochem. Biophysy Res. Comm* 319:264-274, 2004; Cui et al. *Computer Method and Programs in Biomedicine* 75:67-73, 2004, Wang et al., *Bioinformatics* 20:1818-1820, 2004). For example, design of siRNAs (including hairpins) typically follow known thermodynamic rules (see, e.g., Schwarz, et al., *Cell* 115:199-208, 2003; Reynolds et al., *Nat Biotechnol.* 22:326-30, 2004; Khvorova, et al., *Cell* 115:209-16, 2003). Many computer programs are available for selecting regions of c-Kit that are suitable target sites. These include programs available through commercial sources such as Ambion, Dharmacon, Promega, Invitrogen, Ziagen, and GenScript as well as noncommercial sources such as EMBOSS, The Wistar Institute, Whitehead Institute, and others.

For example, design can be based on the following considerations. Typically shorter sequences, i.e., less than about 30 nucleotides are selected. The coding region of the mRNA is usually targeted. The search for an appropriate target sequence optionally begins 50-100 nucleotides downstream of the start codon, as untranslated region binding proteins and/or translation initiation complexes may interfere with the binding of the siRNP endonuclease complex. Some algorithms, e.g., based on the work of Elbashir et al., supra, search for a 23-nt sequence motif AA(N19)TT (N, any nucleotide) (SEQ ID NO:5) and select hits with approx. 50% G/C-content (30% to 70% has also worked in for them). If no suitable sequences are found, the search is extended using the motif NA(N21). The sequence of the sense siRNA corresponds to (N19)TT or N21 (position 3 to 23 of the 23-nt motif), respectively. In the latter case, the 3' end of the sense siRNA is converted to TT.

Other algorithms preferentially select siRNAs corresponding to the target motif NAR(N17)YNN, where R is purine (A, G) and Y is pyrimidine (C, U). The respective 21-nt sense and antisense siRNAs therefore begin with a purine nucleotide and can also be expressed from pol III expression vectors without a change in targeting site; expression of RNAs from pol III promoters is only efficient when the first transcribed nucleotide is a purine.

Other nucleic acids, e.g., ribozymes, antisense, can also be designed based on known principles. For example, Sfold (see, e.g, Ding, et al., *Nucleic Acids Res.* 32 Web Server issue, W135-W141, Ding & Lawrence, *Nucl. Acids Res.* 31: 7280, 7301, 2003; and Ding & Lawrence *Nucl. Acids Res.* 20:1034-1046, 2001) provides programs relating to designing ribozymes and antisense, as well as siRNAs.

Melanoma Treatment and Administration of Pharmaceutical and Vaccine Compositions Inhibitors of c-Kit can be administered to a patient for the treatment of melanoma. As described in detail below, the inhibitors are administered in any suitable manner, optionally with pharmaceutically acceptable carriers. In some embodiments, imatinib mesylate, or enantiomers, prodrug and pharmaceutically acceptable salts thereof, is administered. Imatinib mesylate is available from Novartis (Basel, Switzerland) (Savage, D. G. and Antman, K. H. (2002) N. Engl. J. Med. 346(9):683-93; Mauro, M. J. et al. (2002) J. Clin. Oncol. 20(1):325-34; Schiffer, C. A. (2001) Semin. Oncol. 28(5 Suppl 17):34-9; Demetri, G. D. (2001) Semin. Oncol. 28(5 Suppl 17):19-26; Griffin, J. (2001) Semin. Oncol. 28(5 Suppl 17):3-8; Verweij, J. et al. (2001) Eur. J. Cancer. 37(15):1816-9; Shah, N. P. and Sawyers, C. L. (2001) Curr. Opin. Investig. Drugs. 2(3):422-3). Protocols for the administration of inhibitors such as imatinib mesylate are known (see, e.g, *J Clin Oncol.* 2003 Dec. 1; 21(23): 4342-9) and can be further optimized for melanoma patients based on principles known in the pharmacological arts (*Remington's Pharmaceutical Sciences,* 17th ed., 1989).

Other c-KIT inhibitors are known. For example, compounds having an indoline skeleton were reported as those showing c-Kit kinase inhibitory action (WO 01/45689). There was also a report concerning the inhibitory action on c-Kit kinase by the compounds having a quinazoline skeleton (WO 01/47890). Other known c-kit inhibitors include CT52923, PD173955, XL820, SU11248, and SU5614. Although it may be desirable to use a specific c-KIT inhibitor, c-KIT inhibitors can be administered that also target other receptor tyrosine kinases. For example, SU11248 (Sutent, Pfizer) is a multi-targeted receptor tyrosine kinase inhibitor which targets 3 distinct vascular endothelial growth factor receptor (VEGFR-1, -2, and -3), platelet-derived growth factor receptor alpha and beta (PDGFR-α and -β), KIT receptor tyrosine kinases, and fms-related tyrosine kinase 3/Flk2 (FLT3). Dasatinib (Bristol Myers Squibb, BMS-354825) is a small molecule kinase inhibitor. Dasatinib is also an SRC inhibitor as well as an abl inhibitor.

The inhibitors can be administered to a patient at therapeutically effective doses to prevent, treat, or control melanoma The compounds are administered to a patient in an amount sufficient to elicit an effective protective or therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular c-Kit inhibitors employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

Inhibitors of Gene Expression

In one aspect of the present invention, c-Kit inhibitors can also comprise nucleic acid molecules that inhibit expression of c-Kit. Conventional viral and non-viral based gene transfer methods can be used to introduce nucleic acids encoding engineered c-Kit polypeptides in mammalian cells or target tissues, or alternatively, nucleic acids e.g., inhibitors of c-Kit activity, such as siRNAs, ribozymes, or anti-sense RNAs. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357: 455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

In some embodiments, siRNAs are administered. siRNA therapy is carried out by administering to a patient a siRNA by standard vectors encoding the siRNAs of the invention and/or gene delivery systems such as by delivering the synthetic siRNA molecules. Typically, synthetic siRNA molecules are chemically stabilized to prevent nuclease degradation in vivo. Methods for preparing chemically stabilized RNA molecules are well known in the art. Typically, such molecules comprise modified backbones and nucleotides to prevent the action of ribonucleases. Other modifications are also possible, for example, cholesterol-conjugated siRNAs have shown improved pharmacological properties (see, e.g., Song et al. *Nature Med.* 9:347-351 (2003).

Non-Viral Delivery Methods

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Viral Delivery Methods

The use of RNA or DNA viral based systems for the delivery of inhibitors of c-Kit are known in the art. Conventional viral based systems for the delivery of c-Kit nucleic acid inhibitors can include retroviral, lentivirus, adenoviral, adeno-associated and herpes simplex virus vectors for gene transfer.

In many gene therapy applications, it is desirable that the gene therapy vector be delivered with a high degree of specificity to a particular tissue type, e.g., a pancreas or breast tissue. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human cancer cells expressing human epidermal growth factor receptor. This principle can be extended to other pairs of virus expressing a ligand fusion protein and target cell expressing a receptor. For example, filamentous phage can be engineered to display antibody fragments (e.g., Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism, transfected with c-Kit inhibitor nucleic acids and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can also be administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences,* 17th ed., 1989).

In some embodiments, c-Kit polypeptides and polynucleotides can also be administered as vaccine compositions to stimulate an immune response, typically a cellular (CTL and/or HTL) response. Such vaccine compositions can include, e.g., lipidated peptides (see, e.g., Vitiello, A. et al., *J. Clin. Invest.* 95:341 (1995)), peptide compositions encapsulated in poly(DL-lactide-co-glycolide) ("PLG") microspheres (see, e.g., Eldridge, et al., *Molec. Immunol.* 28:287-294, (1991); Alonso et al., *Vaccine* 12:299-306 (1994); Jones et al., *Vaccine* 13:675-681 (1995)), peptide compositions contained in immune stimulating complexes (ISCOMS) (see, e.g., Takahashi et al., *Nature* 344:873-875 (1990); Hu et al., *Clin Exp Immunol.* 113:235-243 (1998)), multiple antigen peptide systems (MAPs) (see, e.g., Tam, *Proc. Natl. Acad. Sci. U.S.A.* 85:5409-5413 (1988); Tam, *J. Immunol. Methods* 196:17-32 (1996)), peptides formulated as multivalent peptides; peptides for use in ballistic delivery systems, typically crystallized peptides, viral delivery vectors (Perkus, et al., In: *Concepts in vaccine development* (Kaufmann, ed., p. 379, 1996); Chakrabarti, et al., *Nature* 320:535 (1986); Hu et al., *Nature* 320:537 (1986); Kieny, et al., *AIDS Bio/Technology* 4:790 (1986); Top et al., *J. Infect. Dis.* 124:148 (1971); Chanda et al., *Virology* 175:535 (1990)), particles of viral or synthetic origin (see, e.g., Kofler et al., *J. Immunol. Methods.* 192:25 (1996); Eldridge et al., *Sem. Hematol.* 30:16 (1993); Falo et al., *Nature Med.* 7:649 (1995)), adjuvants (Warren et al., *Annu. Rev. Immunol.* 4:369 (1986); Gupta et al., *Vaccine* 11:293 (1993)), liposomes (Reddy et al., *J. Immunol.* 148:1585 (1992); Rock, Immunol. Today 17:131 (1996)), or, naked or particle absorbed cDNA (Ulmer, et al., *Science* 259:1745 (1993); Robinson et al., *Vaccine* 11:957 (1993); Shiver et al., In: *Concepts in vaccine development* (Kaufmann, ed., p. 423, 1996); Cease & Berzofsky, *Annu. Rev. Immunol.* 12:923 (1994) and Eldridge et al., *Sem. Hematol.* 30:16 (1993)). Toxin-targeted delivery technologies, also known as receptor mediated targeting, such as those of Avant Immunotherapeutics, Inc. (Needham, Mass.) may also be used.

Kits for Use in Diagnostic and/or Prognostic Applications

The invention also provides kits for diagnostic or therapeutic applications. For diagnostic/prognostic applications, such kits may include any or all of the following: assay reagents, buffers, c-KIT and/or SHP-2 probes, primers, antibodies, or the like In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Example 1—Examination of the Copy Number Profiles of 103 Primary Melanomas

MAP-kinase and PI3 kinase pathways are activated differently among subtypes of melanoma when tumors are classified according to a combination of UV exposure and anatomic site (Curtin, et al., *New Engl. J. Med.* 353:2135-2147, 2005). Most prominently, while BRAF mutations are highly prevalent (59%) in melanomas occurring on skin without signs of chronic sun-induced damage (non-CSD melanomas), the frequency is very low in melanomas that occur on the palms, soles or subungual sites or (acral mucosa melanomas, respectively). BRAF mutations are also uncommon in melanomas that occur on skin showing evidence of chronic sun-induced damage (CSD melanomas). About 10 to 20% of melanomas of all subtypes activate these pathways by mutation of NRAS, but mutations of both NRAS and BRAF never occur together. These findings raise the critical question of how the MAP kinase pathway might be activated in those tumors that do not have NRAS or BRAF mutations.

Array CGH analysis by Curtin et al., supra, found differences in the characteristics of the DNA copy number aberrations among the melanoma subtypes, with significant differences in the frequency of involvement of several loci. Examination of the copy number profiles of 103 primary melanomas from this study (data available at GEO, http://www.ncbi.nlm.nih.gov/geo/; accession number GSE2631), found gain (10 tumors) or amplification (7 tumors) of chromosome 4p12, FIG. 2. Sixteen of these tumors had been sequenced for BRAF and NRAS and no mutations were found. All 17 tumors were of the acral, mucosal, or CSD subtypes.

Example 2—Immunohistochemistry and In Situ Hybridization for c-Kit

The common region of 4p12 copy number elevation contains several receptor tyrosine kinases (RTK) that are attractive candidate melanoma oncogenes. These include the v-kit Hardy-Zuckerman 4 feline sarcoma viral oncogene homolog c-Kit, the vascular endothelial growth factor receptor KDR and platelet-derived growth factor alpha receptor (PDGFRA). c-Kit is an essential gene for melanocyte survival and development (Chabot, et al., *Nature* 335:88-89, 1988; Geissler, et al., *Cell* 55:185-192, 1988) and subject to oncogenic mutations in a variety of cancer types (Beghini et al., *Cancer* 92:657-662, 2001; Beghini et al., *Blood Cells Molecules and Diseases* 24:262-270, 1998; Isozaki, et al., *Am. J. Path.* 157:1581-1585, 2000; Lux, et al., *Am. J. Path.* 156: 791-795, 2000; Wardelmann, et al., *Mod. Pathology* 15: 125-136, 2002). However, previous investigations have generally dismissed its importance in melanoma because expression appeared to be lost during tumor progression (Lassam & Bickford, *Oncogene* 7: 51-56, 1992; Natali, et al., *Int. J. Cancer* 52: 197-201, 1992; Zakut, et al., *Oncogene* 8: 2221-2229, 1993; Huang, et al., *Oncogene* 13: 2339-2347, 1996; Montone, et al., *Mod. Pathology* 10: 939-944, 1997). KDR is important in angiogenesis (Millauer, et al., *Cell* 72: 835-846, 1993) and in the development of solid tumors (Millauer, et al., *Nature* 367: 576-579, 1994) and is commonly expressed in melanoma (Straume & Akslen, *Am J Pathol* 159: 223-235, 2001). PDGFRA is found to be activated by mutations or small deletions in a subset of gastro-intestinal stroma tumors (GIST) (Heinrich, et al., *Science* 299: 708-710, 2003) and in childhood acute myeloid leukemia (Hiwatari, et al., *Leukemia* 19: 476-477, 2005).

Figure 2:
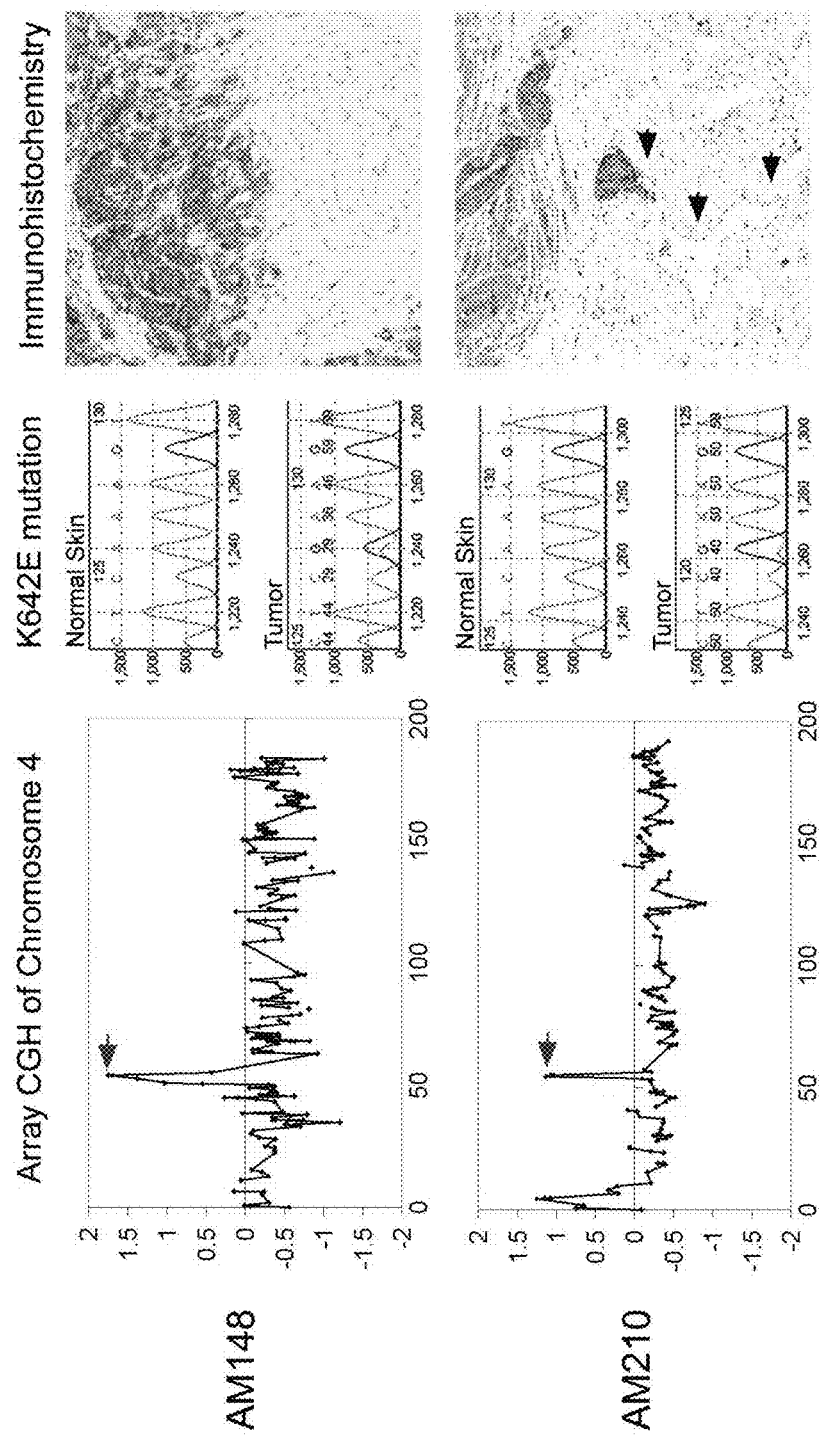
FIG. 2: Two melanomas with amplification, mutation, and overexpression of KIT. The left panel shows the array CGH data with the log 2ratio of the tumor to reference fluorescence intensity on the y-axis and the genomic position of the BAC clones in megabases on the x-axis. A log 2ratio of 0 indicates normal copy number. BAC clones with a ratio greater than 0.9 are considered amplified. The arrows indicate the location of the KIT locus. The middle panels show the sequencing traces of the DNA from the tumor and the adjacent normal tissue. In the tumor DNA, peaks for the mutated allele are higher than the wildtype alleles indicating amplification of the mutated allele. The right panels show strong expression of KIT protein at the invasive front of the melanoma by immunohistochemistry. In case AM210 KIT an aggregate of KIT expressing cells is found in a lymphatic space (arrow heads).

We performed immunohistochemistry for PDGFRA and KDR and in situ hybridization for PDGFRA on tissue microarrays and found that although both genes were expressed in subsets of melanomas, there was no association between copy number increase at 4q12 and protein or RNA expression (data not shown). In addition, sequencing of the common mutation sites of PDGFRA, exons 10, 12, 14 and 18 (Heinrich, et al., *Science* 299: 708-710, 2003), in cases with amplification of 4q12 did not reveal any mutations. In contrast, eight of eleven (73%) melanomas with increased copies of 4q12 that were tested for c-Kit expression using immunohistochemistry employing standard antibody concentrations (see methods) showed increased c-Kit expression. Sequence analysis of the common mutation sites of c-Kit, exons 11, 13, 17 and 18 in the seven samples with amplifications in c-Kit found three samples with mutations. All three samples showed a K642E mutation, and one had an additional mutation at residue N566D (Table 2). The K642E mutation is oncogenic (Isozaki, et al., *Am. J. Path.* 157: 1581-1585, 2000) and occurs in sporadic (Lux, et al., *Am. J. Path.* 156: 791-795, 2000) and familial GISTs (Isozaki, et al., *Am. J. Path.* 157:1581-1585, 2000). The amplification at 4q12 targeted the mutated allele in all three cases, indicated by the peak height of the sequencing traces, and c-Kit protein was highly expressed in all three cases (FIG. 2). These findings indicated that c-Kit was the gene driving the selection of copy number increases at 4q12 in at least these three cases, and motivated sequencing these same c-Kit exons in the remainder of the tumors to determine if mutations were occurring in the absence of copy number changes. Coding mutations in 14 tumors (14%) and an intronic deletion in an additional tumor were found (Table 3). Analysis of DNA from adjacent normal tissue for the c-Kit-mutant cases from which it could be obtained, 8/15, found no mutations, indicating that the mutations were somatically acquired.

The frequencies of c-Kit aberrations (i.e. sequence mutations or copy number increases) in the different melanoma subgroups varied in approximately mirror image with BRAF mutations. c-Kit aberrations in mucosal, acral, CSD, and non-CSD melanomas were present in 39%, 26%, 17% and 0% respectively, while BRAF mutations were present in 11%, 23%, 11%, 59% (Maldonado, et al., *J. Natl. Canc. Inst.* 95: 1878-1880, 2003; Curtin, et al., *New Engl. J. Med.* 353:2135-2147, 2005).

Figure 3:
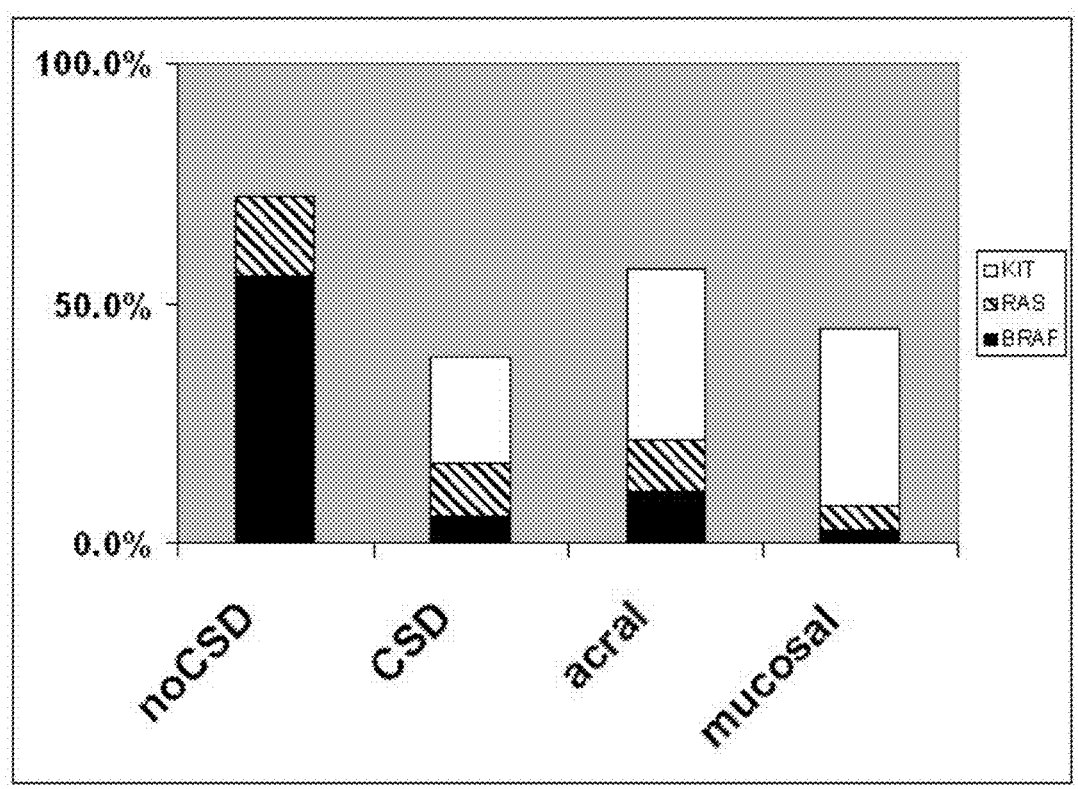
FIG. 3: Frequency distribution of genetic alterations in BRAF, NRAS, and KIT among four groups of melanoma. NoCSD=melanomas on skin without chronic sun-induced damage as evidenced by marked solar elastosis; CSD=melanomas on skin with chronic sun-induced damage as evidenced by marked solar elastosis; acral=melanomas on the soles, palms, or sub-ungual sites; mucosal=melanomas on mucosal membranes.

Immunohistochemical analysis of c-Kit protein expression further supports its role as a melanoma oncogene. Ten out of eleven (91%) melanomas with c-Kit mutations and eight of eleven (73%) with c-Kit copy number increases showed increased expression of c-Kit protein in vertical growth phase (VGP) relative to other portions of the tumor (Table 2, FIG. 1), indicating that c-Kit expression in melanoma is enhanced in the advanced progression stages of the tumors with mutations or dosage increases of the receptor. The four samples with c-Kit mutations or copy number increase that did not show strong c-Kit protein expression in the VGP of the tumor under standard analysis conditions showed enhanced expression in the VGP when higher antibody concentrations were employed. In contrast, only 6/19 (32%) of samples without detectable c-Kit mutation or copy number for which residual tissue was available for immunohistochemistry, showed increased expressed the c-Kit protein in the VGP. Interestingly, the six melanomas that expressed c-Kit in which our methods did not reveal genetic aberrations in c-Kit (n=6) were all wild-type for BRAF or NRAS and only one showed amplification of CCND 1. Thus aberrant c-Kit signaling in melanoma may be activated by both gene dosage effects as described for other cancer types (Sihto, et al., *J Clin Oncol* 23: 49-57, 2005), mutation, and perhaps by other expression-altering mechanisms not measured in our study. The frequencies of c-Kit aberrations (i.e., mutations or copy number increases) in the different melanoma subgroups varied in approximately mirror image with BRAF mutations (e.g., FIG. 3). c-Kit aberrations in mucosal, acral, CSD, and non-CSD melanomas were present in 39%, 26%, 17% and 0% respectively, while BRAF mutations were present in 11%, 23%, 11%, 59% (Maldonado, et al., *J. Natl. Canc. Inst.* 95: 1878-1880, 2003; Curtin, et al., *New Engl. J. Med.* 353:2135-2147, 2005).

We note that our results relative to the importance of c-Kit in melanoma are in contrast with most previous studies, which showed c-Kit to be down-regulated during melanoma progression or to negatively affect tumor growth (Lassam & Bickford, *Oncogene* 7: 51-56, 1992; Natali, et al., *Int. J. Cancer* 52: 197-201, 1992; Zakut, et al., *Oncogene* 8: 2221-2229, 1993; Huang, et al., *Oncogene* 13: 2339-2347, 1996; Montone, et al., *Mod. Pathology* 10: 939-944, 1997). Only one study of metastatic melanomas reports mutations in two out of 100 melanoma metastases without details about the nature of the primary tumor (Willmore-Payne, et al., *Hum. Pathol.* 36: 486-493, 2005). We believe this difference is due to our approach to melanoma classification, which motivated us to use a sample cohort enriched in tumors where c-Kit happened to be active, and to interpret the results in a broader context. Concordant with our findings, high level c-Kit expression was previously reported in acral melanomas (Ohashi, et al., *Melanoma Res.* 6: 25-30, 1996).

Our data have important implications for melanoma therapy, and improving the understanding of melanoma development, and suggesting future lines of research. Most of the mutations we found in melanoma have been reported in other cancer types and are thought to lead to constitutive activation of the receptor (Table 3). Twelve of the melanomas in our series had mutations that affected the juxtamembrane domain which are expected to promote dimerization in the absence of scatter factor (SCF) resulting in constitutive activation (Lennartsson, et al., *Oncogene* 18: 5546-5553, 1999) or to prevent c-Kit from maintaining its auto-inhibited conformation (Mol, et al., *J. Biol. Chem.* 279: 31655-31663, 2004). Importantly for therapeutic considerations, mutations in the juxtamembrane region were most frequent in our series (table) and are potentially responsive to Imatinib (Frost, et al., *Mol. Canc. Ther.* 1: 1115-1124, 2002; Heinrich, et al., *J. Clin. One.* 21: 4342-4349, 2003; Ma, et al., *Blood* 99: 1741-1744, 2002). Three of our cases had mutations in the kinase domain which frequently are resistant to Imatinib (Heinrich, et al., *J. Clin. One.* 21: 4342-4349, 2003) the types of melanoma that contain c-Kit mutations represent a minority of cases in populations of European descent, worldwide they may represent the highest melanoma burden because they are more common in people of African, Asian, and Hispanic descent. In addition they are particularly aggressive, so that the therapeutic impact of knowledge of these mutations may be considerable.

The combination of mutation, dosage, and protein expression data indicate the complexities of the manner in which c-Kit may be involved in aberrant signaling. In our cohort, only melanomas with the K642E mutation showed copy number increase of c-Kit, and conversely this mutation was not found in melanomas without dosage increase or NRAS mutation (e.g., Tables 1 and 2). Functional studies (Tarn, et al., *Clin. Canc. Res.* 11: 3668-3677, 2005) and the finding that the K642E allele can be found in the germline (Isozaki, et al., *Am. J. Path.* 157:1581-1585, 2000) suggests that it represents a weakly activating form of c-Kit. Thus this mutation appears to require additional directly interacting selective steps in order to provide a significant oncogenic signal. All other samples with coding mutations in c-Kit did not have copy number increases of the c-Kit locus and did not show BRAF or NRAS mutations, suggesting that these mutations have a substantially stronger oncogenic signal.

Melanoma types that show frequent genetic alterations of c-Kit frequently show a lentiginous growth pattern, characterized by melanocytes lined up as singles cells along the epidermis in the progression stage preceeding invasive growth. By contrast, non-CSD melanomas typically show a pagetoid growth pattern with melanocytes scattered throughout the epidermis.

Example 2 Analysis of SHP2 Mutations

Methods

We studied 104 primary melanomas from mucosa (n=35), acral skin (n=24), skin with (n=16) and without (n=12) chronic sun-induced damage and ocular melanoma (n=16). Sun-induced damage was defined microscopically by the presence or absence of marked solar elastosis. These cases are part of a previously published data set (Maldonado, et al. *J. Natl. Canc. Inst.* 95:1878-1880, 2003; Curtin, et al., *New Engl. J. Med.* 353:2135-2147, 2005). We also studied 13 cell lines.

DNA for mutation analysis was extracted from formalin fixed, paraffin embedded primary tumors and surrounding normal tissue as published previously (Bastian, et al: *Cancer Res.* 8:2170-2175, 1998). We performed sequence analysis by direct sequencing of PCR amplified products generated with specific primers designed to include the exons of interest. The primers used were as follows (SEQ ID NOS: 6-21):
exon 3a: 5'-gtaaaatccgacgtggaagatg-3' (forward) and 5'-gttcagaggtaggatctgcacagt-3' (reverse);
exon 3b: 5'-gaaatggagctgtcacccacatc-3' (forward) and 5'-catacacagaccgtcatgcattt-3' (reverse);
exon 4a: 5'-tttgtgaaagaacaacatgaacc-3' (forward) and 5'-gacttgccgtcattgctctc-3' (reverse);
exon 4b: 5'-ggaaaacatggtagttttcttgtacg-3' (forward) and 5'-tgaatgtaatggtgtctgtcttctg-3' (reverse);
exon 7: 5'-gtaatgctgatccaggctt-3' (forward) and 5'-ccctgaggaaaggtacagagg-3' (reverse);
exon 8: 5'-gctggggagtaactgatttga-3' (forward) and 5'-ctttcaggacatgaggaagg-3' (reverse);
exon 13a: 5'-gtccactaaaagttgtgcattaaaca-3' (forward) and 5'-caggctggtacctgctcttc-3' (reverse);
exon 13b: 5'-catgatgtttccttcgtaggtg-3' (forward) and 5'-ctcctgctcaaaaggagagc-3' (reverse).

For sequencing purposes, an M13 forward (5'-tgtaaaacgacggccagt-3'; SEQ ID NO:22) and reverse (5'-agcggataacaatttcacacagg-3'; SEQ ID NO:23) primer were added onto the 5' terminals of each forward and reverse primer respectively. The PCR cycling conditions were as follows. An initial denaturation at 95° C. for 6 minutes was followed by ten cycles of 95° C. for 90 seconds, an annealing phase at 62° C. for 90 seconds decreasing by 0.5° C. every cycle to touchdown at 57° C., and an elongation step of 72° C. for 90 seconds. This was followed by an additional 36 cycles as described above with an annealing temperature of 57° C. and finally an elongation step at 72° C. for 10 minutes. PCR products were purified using ExoSAP-IT® (USB Corporation, Cleveland, Ohio) and sequenced directly with M13 primers using an ABI PRISM® 3700 DNA Analyzer (Applied Biosystems, Foster City, Calif.).

SHP2 (also known as PTPN11) encodes the non receptor-type protein tyrosine phosphatase, Src homology region 2-domain phosphatase-2 (SHP-2) and functions as an intracellular signal transducer that associates with tyrosine kinase receptors, and scaffolding adapters (Tartaglia & Gelb, *Ann. Rev. Genom. and Hum. Gen.* 6:45-68, 2005). We sequenced exons 3, 7, 8 and 13 in 104 primary melanoma tumors and 13 melanoma cell lines and exon 4 in 50 primary melanomas and observed three mutations, resulting in a P491L, S150F, and I309V substitution, respectively, both of which occur in the protein tyrosine phosphatase (PTP) domain. They were found in a melanoma on chronically sun-damaged skin (CSD) and in mucosal melanoma, respectively, and were demonstrated to be somatically acquired by sequencing the DNA from adjacent normal tissue.

The P491L substitution (Binder, et al., J Clin Endocrinol Metab 90:5377-5381, 2005 has been found in the germline in patients with Noonan syndrome and somatically acquired in ALL (Tartaglia, et al., *Blood* 104:307-313, 2004). The I309V mutation in the germline also has been observed in Noonan syndrome (Tartaglia, et al., *Am. J. Hum. Gen.* 70:1555-1563, 2002). Somatic and germline mutations resulting in P491L and P491S substitutions and germline mutations resulting in a I309V substitution were also reported in a study examining patients with either Noonan or Leopard syndrome (Tartaglia, et al., *Am J Hum Genet.* 78:279-290, 2006). The S150F has not previously been reported. A mutation resulting in a R138Q mutation in SHP2 has been previously reported in one melanoma sample (Bentires-Alj, et al., *Cancer Res* 64:8816-8820, 2004).

The Shp2 protein consists of a N-SH2, PTP and C-SH2 domain. Although the exact mechanism of the function of SHP2 is not completely clear, it is proposed that in its inactive state the N-SH2 domain blocks the PTP catalytic site. Binding of SHP2 to its ligand activates the phosphatase by changing the conformation of the N-SH2 domain resulting in its dissociation from the PTP domain (Tartaglia & Gelb, *Ann. Rev. Genom. and Hum. Gen.* 6:45-68, 2005). Both the I309 and P491 residues are located in the PTP domain. In its inactive state the SHP2 protein is inactive due to interactions between the PTP and the N—SH2 domain. Crystal structure evidence indicates that the P491 residue is spatially far from the N—SH2/PTP interaction surfaces. Both the I309 and P491 residues are thought to contribute to the overall PTP structure and are not thought to play a role in catalytic function or N-SH2/PTP interactions (Tartaglia, et al., *Am J Hum Genet.* 78:279-290, 2006).

Shp2 positively controls the activation of the RAS/MAPK cascade (Cunnick, et al., *J. Biol. Chem.* 277:9498-9504, 2002; Maroun, et al., *Mol. Cell. Biol.* 20:8513-8525, 2000; Shi, et al., *Mol. Cell. Biol* 20:1526-1536, 2000; Saxton, et al., *Embo J.* 16:2352-2364, 1997). The MAPK pathway is deregulated in JMML due to mutations in NRAS, KRAS2 or NF 1 in approximately 40% of cases. A genetic analysis of SHP2 in 62 JMML patients without Noonan syndrome demonstrated that 34% of JMML patients had mutations in SHP2. Complementing these data with the mutation status of other components of the MAPK pathway demonstrated and mutations of SHP2 were mutually exclusive of other mutations of the MAPK pathway supporting a MAPK pathway activating role for Shp2 (Tartaglia, et al., *Nat Genet.* 34:148-150, 2003).

Figure 4:
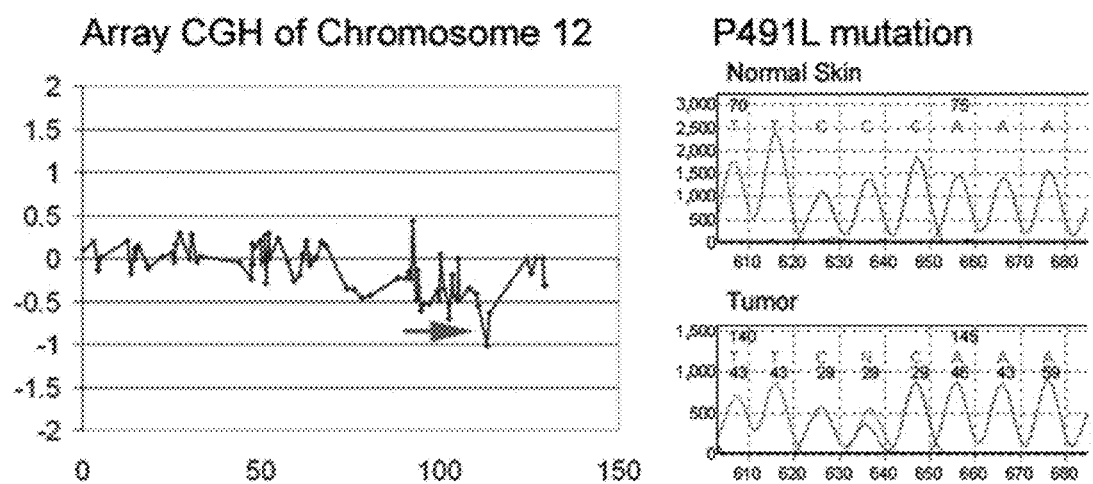
FIG. 4: Loss and mutation of SHP2 in a primary melanoma. The left panel shows the array CGH profile of chromosome 12 for a primary melanoma with a narrow loss of 12q24.13 that contains SHP2 (arrowhead). The Y axis shows the log 2 ratio for each locus normalized to the genome median log 2 ratio. The X-axis shows the genomic position of the loci using data from the UCSC Genome Browser website at genome.ucsc.edu; July 2003 assembly). The right panel shows the sequencing traces of exon 13 of SHP2 showing an C to T transition resulting in a P491L amino acid substitution. The peak height of the sequencing traces indicates that the loss at 12q24.13 target the normal allele.

In the 104 primary melanomas analyzed in this example, two patients had mutations in SHP2. Neither patient had mutations in other components of the MAPK cascade examined, mutation of BRAF, NRAF, KIT or abnormal copy number of KIT. Analysis of published CGH data (Curtin, et al., *New Engl. J. Med* 353:2135-2147, 2005) in our dataset demonstrated that the mutated CSD sample lost a copy of the SHP2 locus and the lost allele targets the wild type allele as indicated by the peak height of the sequencing traces (FIG. 4).

Generally, there is a distinct distribution of mutations in SHP2 in patients with Noonan or Leopard syndrome or JMML, AML indicating that different mutations result in distinct phenotypes. Mutations of SHP2 in JMML which are without associated Noonan, are not found in the germline indicating that these mutation may be lethal. In contrast, somatic mutations in SHP2 that result in Noonan syndrome but are not leukemogenic may have a milder gain-of-function. The authors speculated that Noonan syndrome/JMML mutants have intermediate effects, which may explain the milder course of the JMML when it occurs in Noonan syndrome patients. Individuals with Noonan syndrome who develop juvenile myelomonocytic leukemia (JMML) have germline mutations in SHP2 in 5/7 cases, 4 of theses have mutations resulting in a Thr73Ile substitution whereas this substitution occurs in only 4% of Noonan syndrome patients (Tartaglia, et al., *Nat Genet.* 34:148-150, 2003).

The mutations identified in the two melanoma samples as disclosed in this example are known disease-causing alterations found in syndromes and cancers with MAPK pathway activation. Our observation that these mutations occur in melanomas without additional activations in the MAPK pathway suggests that Shp2 mutation, provides an alternate mechanism of MAPK activation in melanoma. Under normal physiological conditions the MAPK pathway can be activated by stem cell factor (SCF) binding to receptor tyrosine kinase KIT resulting in dimerization of KIT and therefore activation of its protein kinase activity (Roskoski, *Biochem. Biophys. Res. Comm.* 337:1-13, 2005). This results in autophosphorylation of KIT at tyrosine residues that are docking sites for signal transduction molecules containing SH2 domains. SHP2 is known to bind to the phosphotyrosine 568 of KIT (Roskoski, Biochem. Biophys. Res. Comm. 337:1-13, 2005). In melanoma KIT is frequently mutated in tumors without mutation of *BRAF* (Curtin, et al., *J Clin Oncol* 24:4340-4346, 2006) resulting in MAPK activation. Cancers with mutations in the juxta-membrane region of KIT are responsive to Imatinib (Heinrich, et al., *J Clin Oncol.* 21:4342-4349, 2003; Frost, et al, *Mol Canc Therap* 1:1115-1124, 2002; Ma, et al., *Blood* 99:1741-1744, 2002), since these mutations are expected to promote KIT dimerization in the absence of SCF resulting in its constitutive activation (Lennartsson, et al., *Oncogene* 18:5546-5553, 1999), or to prevent KIT from maintaining its auto-inhibited conformation (Mol, et al., J Biol. Chem. 279:31655-31663, 2004). Imatinib prevents the autophosphorylation of KIT (Heinrich, et al., *Blood* 96:925-932, 2000), thus indicating a therapeutic effect for agents such as Imatinib for tumors with SHP2 mutations, as its docking site on KIT will not be autophosphorylated and therefore SHP2 will be unable to positively activate the MAPK pathway.

The above examples are provided by way of illustration only and not by way of limitation. Those of skill in the art will readily recognize a variety of noncritical parameters that could be changed or modified to yield essentially similar results.

All publications and patent applications cited in this specification are herein incorporated by reference as if each individual publication or patent application were specifically and individually indicated to be incorporated by reference.

TABLE 1

|  | No. of mutated BRAF (%) | No. of mutated RAS (%) | No. of mutated KIT (%) | No. with Kit increased copy number (%) |
| --- | --- | --- | --- | --- |
| noCSD | 22/33 (67) | 8/33 (24) | 3/18 (0) | 0/36 (0) |
| CSD | 3/26 (12) | 4/26 (15) | 4/19 (21) | 1/29 (3) |
| Mucosal | 2/31 (6) | 1/30 (3) | 8/37 (22) | 10/33 (30) |
| Acral | 6/31 (19) | 3/31 (10) | 3/29 (10) | 6/34 (18) |

TABLE 2

| Code | Type | Kit copy number | Kit Mutation | Immunohistochemistry |
| --- | --- | --- | --- | --- |
| 20 | acral | amp | wt | na |
| AM108 | acral | amp | wt | positive |
| AM107 | acral | enh | wt | na |
| AM126 | acral | enh | wt | positive[1] |
| AM130 | acral | enh | wt | positive |
| AM112 | acral | normal | wt | na |
| AM169 | acral | normal | Y553N | positive[1] |
| AM17 | acral | normal | R634W | positive |
| AM60 | acral | normal | K642E and BRAF | positive |
| AM141 | mucosal | amp | K642E | positive |
| AM148 | mucosal | amp | K642E | positive |
| AM218 | mucosal | amp | wt | positive[1] |
| AM210 | mucosal | amp | K642E and N566D | positive |
| AM120 | mucosal | enh | wt | positive |
| AM209 | mucosal | enh | wt | positive |
| AM157 | mucosal | enh | wt | na |
| AM147 | mucosal | enh | wt | positive[1] |

TABLE 2-continued

| Code | Type | Kit copy number | Kit Mutation | Immunohistochemistry |
| --- | --- | --- | --- | --- |
| AM143 | mucosal | enh | wt | positive |
| AM124 | mucosal | enh | wt | na |
| AM223 | mucosal | normal | V559A | positive |
| AM219 | mucosal | na | V559A | positive |
| AM207 | mucosal | na | L576P | positive |
| AM220 | mucosal | na | L576P | positive |
| AM150 | mucosal | normal | D816H | positive |
| 111 | CSD | amp | wt | na |
| 53 | CSD | normal | L576P | na |
| Mx41 | CSD | normal | D816H | na |
| 18 | CSD | normal | A829P | na |
| 57 | CSD | normal | intronic deletion/ NRAS | na | enh: increased copy no.;
amp: amplification;
na: not available;
CSD: chronic sun damage
[1]CD117 staining performed at a concentration of 1/25 for 60 minutes

TABLE 3

| Kit Mutation | No. of mutations | Domain affected | Disease mutation is reported |
| --- | --- | --- | --- |
| K642E | 4 | JMD[1] | germ cell tumor |
| L576P | 3 | JMD | GIST |
| D816H | 2 | Kinase | AML, germ cell tumor |
| V559A | 2 | JMD | GIST |
| A829P | 1 | Kinase | novel |
| intronic deletion | 1 | JMD | novel |
| R634W | 1 |  | novel |
| Y553N | 1 | JMD | novel but many mutations at 550-556 in GIST |
| N566D | 1 | JMD | GIST (N566G) |

JMD is juxtamembrane
[1]residue is located outside the JMD, but the mutation is known to destabilize the JMD through amino acid interactions SEQ ID NO: 1
exemplary human KIT nucleic acid sequence CDS 22-2952

```
  1 gatcccatcg cagctaccgc gatgagaggc gctcgcggcg cctgggattt tctctgcgtt
 61 ctgctcctac tgcttcgcgt ccagacaggc tcttctcaac catctgtgag tccaggggaa
121 ccgtctccac catccatcca tccaggaaaa tcagacttaa tagtccgcgt gggcgacgag
181 attaggctgt tatgcactga tccgggcttt gtcaaatgga cttttgagat cctggatgaa
241 acgaatgaga ataagcagaa tgaatggatc acggaaaagg cagaagccac caacaccggc
301 aaatacacgt gcaccaacaa acacggctta agcaattcca tttatgtgtt tgttagagat
361 cctgccaagc ttttccttgt tgaccgctcc ttgtatggga agaagacaa cgacacgctg
421 gtccgctgtc ctctcacaga cccagaagtg accaattatt ccctcaaggg gtgccagggg
481 aagcctcttc caaggactt gaggtttatt cctgacccca aggcgggcat catgatcaaa
541 agtgtgaaac gcgcctacca tcggctctgt ctgcattgtt ctgtggacca ggagggcaag
601 tcagtgctgt cggaaaaatt catcctgaaa gtgaggccag ccttcaaagc tgtgcctgtt
661 gtgtctgtgt ccaaagcaag ctatcttctt agggaagggg aagaattcac agtgacgtgc
721 acaataaaag atgtgtctag ttctgtgtac tcaacgtgga aaagagaaaa cagtcagact
781 aaactacagg agaaatataa tagctggcat cacggtgact tcaattatga acgtcaggca
841 acgttgacta tcagttcagc gagagttaat gattctggag tgttcatgtg ttatgccaat
```

-continued

```
 901 aatactttg gatcagcaaa tgtcacaaca accttggaag tagtagataa aggattcatt 961 aatatcttcc ccatgataaa cactacagta tttgtaaacg atggagaaaa tgtagatttg 1021 attgttgaat atgaagcatt ccccaaacct gaacaccagc agtggatcta tatgaacaga 1081 accttcactg ataaatggga agattatccc aagtctgaga atgaaagtaa tatcagatac 1141 gtaagtgaac ttcatctaac gagattaaaa ggcaccgaag gaggcactta cacattccta 1201 gtgtccaatt ctgacgtcaa tgctgccata gcatttaatg tttatgtgaa tacaaaacca 1261 gaaatcctga cttacgacag gctcgtgaat ggcatgctcc aatgtgtggc agcaggattc 1321 ccagagccca caatagattg gtattttgt ccaggaactg agcagagatg ctctgcttct 1381 gtactgccag tggatgtgca gacactaaac tcatctgggc caccgtttgg aaagctagtg 1441 gttcagagtt ctatagattc tagtgcattc aagcacaatg gcacggttga atgtaaggct 1501 tacaacgatg tgggcaagac ttctgcctat tttaactttg catttaaagg taacaacaaa 1561 gagcaaatcc atccccacac cctgttcact cctttgctga ttggtttcgt aatcgtagct 1621 ggcatgatgt gcattattgt gatgattctg acctacaaat atttacagaa acccatgtat 1681 gaagtacagt ggaaggttgt tgaggagata aatggaaaca attatgttta catagaccca 1741 acacaacttc cttatgatca caaatgggag tttcccagaa acaggctgag ttttgggaaa 1801 accctgggtg ctggagcttt cgggaaggtt gttgaggcaa ctgcttatgg cttaattaag 1861 tcagatgcgg ccatgactgt cgctgtaaag atgctcaagc cgagtgccca tttgacagaa 1921 cgggaagccc tcatgtctga actcaaagtc ctgagttacc ttggtaatca catgaatatt 1981 gtgaatctac ttggagcctg caccattgga gggcccaccc tggtcattac agaatattgt 2041 tgctatggtg atcttttgaa ttttttgaga agaaaacgtg attcatttat ttgttcaaag 2101 caggaagatc atgcagaagc tgcactttat aagaatcttc tgcattcaaa ggagtcttcc 2161 tgcagcgata gtactaatga gtacatggac atgaaacctg gagtttctta tgttgtccca 2221 accaaggccg acaaaaggag atctgtgaga ataggctcat acatagaaag agatgtgact 2281 cccgccatca tggaggatga cgagttggcc ctagacttag aagacttgct gagcttttct 2341 taccaggtgg caaagggcat ggcttttcctc gcctccaaga attgtattca cagagacttg 2401 gcagccagaa atatcctcct tactcatggt cggatcacaa agatttgtga ttttggtcta 2461 gccagagaca tcaagaatga ttctaattat gtggttaaag aaacgctcg actacctgtg 2521 aagtggatgg cacctgaaag cattttcaac tgtgtataca cgtttgaaag tgacgtctgg 2581 tcctatggga ttttcttg ggagctgttc tctttaggaa gcagcccta tcctggaatg 2641 ccggtcgatt ctaagttcta caagatgatc aaggaaggct tccggatgct cagccctgaa 2701 cacgcacctg ctgaaatgta tgacataatg aagacttgct gggatgcaga tccctaaaa 2761 agaccaacat tcaagcaaat tgttcagcta attgagaagc agatttcaga gagcaccaat 2821 catatttact ccaacttagc aaactgcagc cccaaccgac agaagcccgt ggtagaccat 2881 tctgtgcgga tcaattctgt cggcagcacc gcttcctcct cccagcctct gcttgtgcac 2941 gacgatgtct gagcagaatc agtgtttggg tcacccctcc aggaatgatc tcttcttttg 3001 gcttccatga tggttatttt cttttctttc aacttgcatc caactccagg atagtgggca 3061 ccccactgca atcctgtctt tctgagcaca ctttagtggc cgatgatttt tgtcatcagc 3121 caccatccta ttgcaaaggt tccaactgta tatattccca atagcaacgt agcttctacc 3181 atgaacagaa acattctga tttggaaaaa gagagggagg tatggactgg gggccagagt 3241 cctttccaag gcttctccaa ttctgcccaa aaatatggtt gatagtttac ctgaataaat
```

-continued

```
3301 ggtagtaatc acagttggcc ttcagaacca tccatagtag tatgatgata caagattaga
3361 agctgaaaac ctaagtcctt tatgtggaaa acagaacatc attagaacaa aggacagagt
3421 atgaacacct gggcttaaga aatctagtat ttcatgctgg aatgagaca taggccatga
3481 aaaaaatgat ccccaagtgt gaacaaaaga tgctcttctg tggaccactg catgagcttt
3541 tatactaccg acctggtttt taaatagagt ttgctattag agcattgaat tggagagaag
3601 gcctccctag ccagcacttg tatatacgca tctataaatt gtccgtgttc atacatttga
3661 ggggaaaaca ccataaggtt tcgtttctgt atacaaccct ggcattatgt ccactgtgta
3721 tagaagtaga ttaagagcca tataagtttg aaggaaacag ttaataccat tttttaagga
3781 aacaatataa ccacaaagca cagtttgaac aaaatctcct cttttagctg atgaacttat
3841 tctgtagatt ctgtggaaca agcctatcag cttcagaatg gcattgtact caatggattt
3901 gatgctgttt gacaaagtta ctgattcact gcatggctcc cacaggagtg ggaaaacact
3961 gccatcttag tttggattct tatgtagcag gaaataaagt ataggtttag cctccttcgc
4021 aggcatgtcc tggacaccgg gccagtatct atatatgtgt atgtacgttt gtatgtgtgt
4081 agacaaatat ttggagggt attttttgccc tgagtccaag agggtccttt agtacctgaa
4141 aagtaacttg gctttcatta ttagtactgc tcttgtttct tttcacatag ctgtctagag
4201 tagcttacca gaagcttcca tagtggtgca gaggaagtgg aaggcatcag tccctatgta
4261 tttgcagttc acctgcactt aaggcactct gttatttaga ctcatcttac tgtacctgtt
4321 ccttagacct tccataatgc tactgtctca ctgaaacatt taaattttac cctttagact
4381 gtagcctgga tattattctt gtagtttacc tcttttaaaaa caaacaaaa caaaacaaaa
4441 aactcccctt cctcactgcc aatataaaa ggcaaatgtg tacatggcag agtttgtgtg
4501 ttgtcttgaa agattcaggt atgttgcctt tatggtttcc cccttctaca tttcttagac
4561 tacatttaga gaactgtggc cgttatctgg aagtaaccat ttgcactgga gttctatgct
4621 ctcgcacctt tccaaagtta acagattttg gggttgtgtt gtcacccaag agattgttgt
4681 ttgccatact ttgtctgaaa aattcctttg tgtttctatt gacttcaatg atagtaagaa
4741 aagtggttgt tagttataga tgtctaggta cttcaggggc acttcattga gagttttgtc
4801 ttgccatact ttgtctgaaa aattcctttg tgtttctatt gacttcaatg atagtaagaa
4861 aagtggttgt tagttataga tgtctaggta cttcaggggc acttcattga gagttttgtc
4921 aatgtctttt gaatattccc aagcccatga gtccttgaaa atatttttta tatatacagt
4981 aactttatgt gtaaatacat aagcggcgta agtttaaagg atgttggtgt tccacgtgtt
5041 ttattcctgt atgttgtcca attgttgaca gttctgaaga attc
```

SEQ ID NO: 2
exemplary c-Kit human polypeptide sequence
```
  1 mrgargawdf lcvllllrv qtgssqpsvs pgepsppsih pgksdlivrv gdeirllctd
 61 pgfvkwtfei ldetnenkqn ewitekaeat ntgkytctnk hglsnsiyvf vrdpaklflv
121 drslygkedn dtlvrcpltd pevtnyslkg cqgkplpkdl rfipdpkagi miksvkrayh
181 rlclhcsvdq egksvlsekf ilkvrpafka vpvvsyskas yllregeeft vtctikdvss
241 svystwkren sqtklqekyn swhhgdfnye rqatltissa rvndsgvfmc yanntfgsan
301 vtttlevvdk gfinifpmin ttvfvndgen vdliveyeaf pkpehqqwiy mnrtftdkwe
361 dypksenesn iryvselhlt rlkgteggty tflvsnsdvn aaiafnvyvn tkpeiltydr
421 lvngmlqcva agfpeptidw yfcpgteqrc sasvlpvdvq tlnssgppfg klvvqssids
481 safkhngtve ckayndvgkt sayfnfafkg nnkeqihpht lftplligfv ivagmmciiv
541 miltykylqk pmyevqwkvv eeingnnyvy idptqlpydh kwefprnrls fgktlgagaf
```

```
601 gkvveatayg liksdaamtv avkmlkpsah lterealmse lkvlsylgnh mnivnllgac 661 tiggptivit eyccygdlln flrrkrdsfi cskqedhaea alyknllhsk esscsdstne 721 ymdmkpgvsy vvptkadkrr svrigsyier dvtpaimedd elaldledll sfsyqvakgm 781 aflaskncih rdlaarnill thgritkicd fglardiknd snyvvkgnar lpvkwmapes 841 ifncvytfes dvwsygiflw elfslgsspy pgmpvdskfy kmikegfrml spehapaemy 901 dimktcwdad plkrptfkqi vgliekqise stnhiysnla ncspnrqkpv vdhsvrinsv 961 gstasssqpl lvhddv
```

SEQ ID NO: 3
exemplary human SHP2 nucleic acid sequence NM_002834

```
   1 atgacatcgc ggagatggtt tcacccaaat atcactggtg tggaggcaga aaacctactg 61 ttgacaagag gagttgatgg cagtttttg gcaaggccta gtaaaagtaa ccctggagac 121 ttcacacttt ccgttagaag aaatggagct gtcacccaca tcaagattca gaacactggt 181 gattactatg acctgtatgg aggggagaaa tttgccactt ggctgagtt ggtccagtat 241 tacatggaac atcacgggca attaaaagag aagaatggag atgtcattga gcttaaatat 301 cctctgaact gtgcagatcc tacctctgaa ggtggtttc atggacatct ctctgggaaa 361 gaagcagaga aattattaac tgaaaaagga aaacatggta gttttcttgt acgagagagc 421 cagagccacc ctggagattt tgttctttct gtgcgcactg gtgatgacaa aggggagagc 481 aatgacggca agtctaaagt gacccatgtt atgattcgct gtcaggaact gaaatacgac 541 gttggtggag gagaacggtt tgattctttg acagatcttg tggaacatta taagaagaat 601 cctatggtgg aaacattggg tacagtacta caactcaagc agccccttaa cacgactcgt 661 ataaatgctg ctgaaataga aagcagagtt cgagaactaa gcaaattagc tgagaccaca 721 gataaagtca acaaggctt tgggaagaa tttgagacac tacaacaaca ggagtgcaaa 781 cttctctaca gccgaaaaga gggtcaaagg caagaaaaca aaacaaaaa tagatataaa 841 aacatcctgc cctttgatca taccagggtt gtcctacacg atggtgatcc caatgagcct 901 gtttcagatt acatcaatgc aaatatcatc atgcctgaat ttgaaaccaa gtgcaacaat 961 tcaaagccca aaagagtta cattgccaca caaggctgcc tgcaaaacac ggtgaatgac 1021 ttttggcgga tggtgttcca agaaaactcc cgagtgattg tcatgacaac gaaagaagtg 1081 gagagaggaa agagtaaatg tgtcaaatac tggcctgatg agtatgctct aaaagaatat 1141 ggcgtcatgc gtgttaggaa cgtcaaagaa agcgccgctc atgactatac gctaagagaa 1201 cttaaacttt caaaggttgg acaagggaat acggagagaa cggtctggca taccactttt 1261 cggacctggc cggaccacgg cgtgcccagc gaccctgggg gcgtgctgga cttcctggag 1321 gaggtgcacc ataagcagga gagcatcatg gatgcagggc cggtcgtggt gcactgcagt 1381 gctggaattg gccggacagg gacgttcatt gtgattgata ttcttattga catcatcaga 1441 gagaaaggtg ttgactgcga tattgacgtt cccaaaacca tccagatggt gcggtctcag 1501 aggtcaggga tggtccagac agaagcacag taccgattta tctatatggc ggtccagcat 1561 tatattgaaa cactacagcg caggattgaa gaagagcaga aaagcaagag gaaagggcac 1621 gaatatacaa atattaagta ttctctagcg gaccagacga gtggagatca gagccctctc 1681 ccgccttgta ctccaacgcc accctgtgca gaaatgagag aagacagtgc tagagtctat 1741 gaaaacgtgg gcctgatgca acagcagaaa agtttcagat ga
```

-continued

SEQ ID NO: 4
exemplary human SHP2 polypeptide sequence NP_002825
  1 mtsrrwfhpn itgveaenll ltrgvdgsfl arpsksnpgd ftlsvrrnga vthikiqntg 61 dyydlyggek fatlaelvqy ymehhgqlke kngdvielky plncadptse rwfhghlsgk 121 eaeklltekg khgsflvres qshpgdfvls vrtgddkges ndgkskvthv mircqelkyd 181 vggerfdsl tdlvehykkn pmvetlgtvl qlkqplnttr inaaeiesrv relsklaett 241 dkvkqgfwee fetlqqqeck llysrkegqr qenknknryk nilpfdhtrv vlhdgdpnep 301 vsdyinanii mpefetkcnn skpkksyiat qgclqntvnd fwrmvfqens rvivmttkev 361 ergkskcvky wpdeyalkey gvmrvrnvke saandytlre lklskvgqgn tertvwqyhf 421 rtwpdhgvps dpggvldfle evhhkqesim dagpvvvhcs agigrtgtfi vidilidiir 481 ekgvdcdidv pktiqmvrsq rsgmvqteaq yrfiymavqh yietlqrrie eeqkskrkgh 541 eytnikysla dqtsgdqspl ppctptppca emredsarvy envglmqqqk sfr

What is claimed is:

1. A method of treating a human patient that has an acral melanoma or a melanoma that arose from skin having chronic sun-induced damage, the method comprising:

performing a polymerase chain reaction amplification reaction using c-KIT-specific primers on a nucleic acid sample obtained from the melanoma to produce an amplified product comprising a codon encoding the amino acid at position 576 of c-Kit as specified with reference to SEQ ID NO:2;

sequencing the amplified product comprising the codon encoding the amino acid at position 576 in a sequencing reaction;

detecting the presence of a CTT to CCT mutation in the codon encoding position 576, which mutation results in a L576P substitution; and treating the patient with a tyrosine kinase inhibitor.

2. A method of treating a human patient that has an acral melanoma or a melanoma that arose from skin having chronic sun-induced damage, the method comprising:

performing a polymerase chain reaction amplification reaction using c-KIT-specific primers on a nucleic acid sample obtained from the melanoma to produce an amplified product comprising a codon encoding the amino acid at position 576 of c-Kit as specified with reference to SEQ ID NO:2;

hybridizing the amplified product to a probe that selectively hybridizes to a c-KIT gene having a mutation CTT to CCT in the codon encoding the amino acid at position 576 that results in a L576P substitution under conditions in which the probe is selective for binding to the c-KIT gene comprising the mutation and does not bind to a wildtype c-KIT gene;

detecting hybridization of the probe to the amplified product; and treating the patient with a tyrosine kinase inhibitor.

3. A method of treating a human patient that has an acral melanoma or a melanoma that arose from skin having chronic sun-induced damage, the method comprising the steps of:

detecting, in the acral melanoma or the melanoma that arose from skin having chronic sun-induced damage, a c-KIT gene having a mutation CTT to CCT in the codon encoding the amino acid at position 576 of c-Kit as specified with reference to SEQ ID NO:2 by:

obtaining or having obtained a nucleic acid sample from the acral melanoma or the melanoma that arose from skin having chronic sun-induced damage; and performing or having performed sequencing of nucleic acids from the acral melanoma or the melanoma that arose from skin having chronic sun-induced damage; and administering a tyrosine kinase inhibitor.

4. A method of treating a human patient that has an acral melanoma or a melanoma that arose from skin having chronic sun-induced damage, the method comprising the steps of:

detecting, in the acral melanoma or the melanoma that arose from skin having chronic sun-induced damage, a c-KIT gene having a mutation CTT to CCT in the codon encoding the amino acid at position 576 of c-Kit as specified with reference to SEQ ID NO:2 by:

obtaining or having obtained a nucleic acid sample from the acral melanoma or the melanoma that arose from skin having chronic sun-induced damage;

performing or having performed a hybridization assay to nucleic acids from the acral melanoma or the melanoma that arose from skin having chronic sun-induced damage using a probe that selectively hybridizes to a c-KIT gene having the mutation CTT to CCT in the codon encoding the amino acid at position 576 melanoma, but does not bind to a wildtype c-KIT gene; and administering a tyrosine kinase inhibitor.

* * * * *

SEQUENCE LISTING

<160> NUMBER OF SEQ ID NOS: 23

<210> SEQ ID NO 1
<211> LENGTH: 5084
<212> TYPE: DNA
<213> ORGANISM: Homo sapiens
<220> FEATURE:
<223> OTHER INFORMATION: human v-kit Hardy-Zuckerman 4 feline sarcoma
      viral oncogene homolog (c-kit, KIT), mast/stem cell
      growth factor receptor (SCFR), PBT, CD117, YB5.B8
      antigen

<400> SEQUENCE: 1

```
gatcccatcg cagctaccgc gatgagaggc gctcgcggcg cctgggattt tctctgcgtt      60
ctgctcctac tgcttcgcgt ccagacaggc tcttctcaac catctgtgag tccaggggaa     120
ccgtctccac catccatcca tccaggaaaa tcagacttaa tagtccgcgt gggcgacgag     180
attaggctgt tatgcactga tccgggcttt gtcaaatgga cttttgagat cctggatgaa     240
acgaatgaga ataagcagaa tgaatggatc acggaaaagg cagaagccac caacacccgc     300
aaatacacgt gcaccaacaa acacggctta agcaattcca tttatgtgtt tgttagagat     360
cctgccaagc ttttccttgt tgaccgctcc ttgtatggga agaagacaa cgacacgctg     420 gtccgctgtc ctctcacaga cccagaagtg accaattatt ccctcaaggg gtgccagggg     480
aagcctcttc ccaaggactt gaggtttatt cctgacccca aggcgggcat catgatcaaa     540
agtgtgaaac gcgcctacca tcggctctgt ctgcattgtt ctgtggacca ggagggcaag     600
tcagtgctgt cggaaaaatt catcctgaaa gtgaggccag ccttcaaagc tgtgcctgtt     660
gtgtctgtgt ccaaagcaag ctatcttctt agggaagggg aagaattcac agtgacgtgc     720
acaataaaag atgtgtctag ttctgtgtac tcaacgtgga aaagagaaaa cagtcagact     780
aaactacagg agaaatataa tagctggcat cacggtgact tcaattatga acgtcaggca     840
acgttgacta tcagttcagc gagagttaat gattctggag tgttcatgtg ttatgccaat     900 aatactttg atcagcaaa tgtcacaaca accttgaag tagtagataa aggattcatt     960
aatatcttcc ccatgataaa cactacagta tttgtaaacg atggagaaaa tgtagatttg    1020
attgttgaat atgaagcatt ccccaaacct gaacaccagc agtggatcta tatgaacaga    1080
accttcactg ataaatggga agattatccc aagtctgaga atgaaagtaa tatcagatac    1140
```

```
gtaagtgaac ttcatctaac gagattaaaa ggcaccgaag gaggcactta cacattccta    1200
gtgtccaatt ctgacgtcaa tgctgccata gcatttaatg tttatgtgaa tacaaaacca    1260
gaaatcctga cttacgacag gctcgtgaat ggcatgctcc aatgtgtggc agcaggattc    1320
ccagagccca caatagattg gtattttgt ccaggaactg agcagagatg ctctgcttct     1380
gtactgccag tggatgtgca gacactaaac tcatctgggc caccgtttgg aaagctagtg    1440
gttcagagtt ctatagattc tagtgcattc aagcacaatg gcacggttga atgtaaggct    1500
tacaacgatg tgggcaagac ttctgcctat tttaactttg catttaaagg taacaacaaa    1560
gagcaaatcc atcccacac cctgttcact cctttgctga ttggtttcgt aatcgtagct     1620
ggcatgatgt gcattattgt gatgattctg acctacaaat atttacagaa acccatgtat    1680
gaagtacagt ggaaggttgt tgaggagata aatggaaaca attatgttta catagaccca    1740
acacaacttc cttatgatca caaatgggag tttcccagaa acaggctgag ttttgggaaa    1800
accctgggtg ctggagcttt cgggaaggtt gttgaggcaa ctgcttatgg cttaattaag    1860
tcagatgcgg ccatgactgt cgctgtaaag atgctcaagc cgagtgccca tttgacagaa    1920
cgggaagccc tcatgtctga actcaaagtc ctgagttacc ttggtaatca catgaatatt    1980
gtgaatctac ttggagcctg caccattgga gggcccaccc tggtcattac agaatatgt    2040 tgctatggtg atctttgaa tttttgaga agaaaacgtg attcatttat ttgttcaaag      2100
caggaagatc atgcagaagc tgcactttat aagaatcttc tgcattcaaa ggagtcttcc    2160
tgcagcgata gtactaatga gtacatggac atgaaacctg agtttcta tgttgtccca      2220 accaaggccg acaaaaggag atctgtgaga ataggctcat acatagaaag agatgtgact    2280
cccgccatca tggaggatga cgagttggcc ctagacttag aagacttgct gagcttttct    2340
taccaggtgg caaagggcat ggcttttcctc gcctccaaga attgtattca cagagacttg    2400
gcagccagaa atatcctcct tactcatggt cggatcacaa agatttgtga ttttggtcta    2460
gccagagaca tcaagaatga ttctaattat gtggttaaag gaaacgctcg actacctgtg    2520
aagtggatgg cacctgaaag cattttcaac tgtgtataca cgtttgaaag tgacgtctgg    2580
tcctatggga tttttctttg ggagctgttc tcttaggaa gcagcccta tcctggaatg      2640 ccggtcgatt ctaagttcta caagatgatc aaggaaggct tccggatgct cagccctgaa    2700
cacgcacctg ctgaaatgta tgacataatg aagacttgct gggatgcaga tcccctaaaa    2760
agaccaacat tcaagcaaat tgttcagcta attgagaagc agatttcaga gagcaccaat    2820
catatttact ccaacttagc aaactgcagc cccaaccgac agaagcccgt ggtagaccat    2880
tctgtgcgga tcaattctgt cggcagcacc gcttcctcct cccagcctct gcttgtgcac    2940
gacgatgtct gagcagaatc agtgtttggg tcacccctcc aggaatgatc tcttcttttg    3000
gcttccatga tggttatttt cttttctttc aacttgcatc caactccagg atagtgggca    3060
ccccactgca atcctgtctt tctgagcaca ctttagtggc cgatgatttt tgtcatcagc    3120
caccatccta ttgcaaaggt tccaactgta tatattccca atagcaacgt agcttctacc    3180
atgaacagaa acattctga tttggaaaaa gagagggagg tatggactgg gggccagagt     3240
cctttccaag gcttctccaa ttctgcccaa aaatatggtt gatagtttac ctgaataaat    3300
ggtagtaatc acagttggcc ttcagaacca tccatagtag tatgatgata caagattaga    3360
agctgaaaac ctaagtcctt tatgtggaaa acagaacatc attagaacaa aggacagagt    3420
atgaacacct gggcttaaga aatctagtat ttcatgctgg gaatgagaca taggccatga    3480
aaaaaatgat ccccaagtgt gaacaaaaga tgctcttctg tggaccactg catgagcttt    3540
```

-continued

```
tatactaccg acctggtttt taaatagagt ttgctattag agcattgaat tggagagaag    3600
gcctccctag ccagcacttg tatatacgca tctataaatt gtccgtgttc atacatttga    3660
ggggaaaaca ccataaggtt tcgtttctgt atacaaccct ggcattatgt ccactgtgta    3720
tagaagtaga ttaagagcca tataagtttg aaggaaacag ttaataccat tttttaagga    3780
aacaatataa ccacaaagca cagtttgaac aaaatctcct cttttagctg atgaacttat    3840
tctgtagatt ctgtggaaca agcctatcag cttcagaatg gcattgtact caatggattt    3900
gatgctgttt gacaaagtta ctgattcact gcatggctcc cacaggagtg gaaaacact     3960 gccatcttag tttggattct tatgtagcag gaaataaagt ataggtttag cctccttcgc    4020
aggcatgtcc tggacaccgg gccagtatct atatatgtgt atgtacgttt gtatgtgtgt    4080 agacaaaatat ttggaggggt attttttgccc tgagtccaag agggtccttt agtacctgaa    4140
aagtaacttg gctttcatta ttagtactgc tcttgtttct tttcacatag ctgtctagag    4200
tagcttacca gaagcttcca tagtggtgca gaggaagtgg aaggcatcag tccctatgta    4260
tttgcagttc acctgcactt aaggcactct gttatttaga ctcatcttac tgtacctgtt    4320
ccttagacct tccataatgc tactgtctca ctgaaacatt taaattttac cctttagact    4380
gtagcctgga tattattctt gtagtttacc tctttaaaaa caaaacaaaa caaaacaaaa    4440 aactccccctt cctcactgcc caatataaaa ggcaaatgtg tacatggcag agtttgtgtg    4500
ttgtcttgaa agattcaggt atgttgcctt tatggtttcc cccttctaca tttcttagac    4560
tacatttaga gaactgtggc cgttatctgg aagtaaccat ttgcactgga gttctatgct    4620 ctcgcaccctt tccaaagtta acagatttttg gggttgtgtt gtcacccaag agattgttgt    4680
ttgccatact ttgtctgaaa aattcctttg tgtttctatt gacttcaatg atagtaagaa    4740
aagtggttgt tagttataga tgtctaggta cttcaggggc acttcattga gagttttgtc    4800
ttgccatact ttgtctgaaa aattcctttg tgtttctatt gacttcaatg atagtaagaa    4860
aagtggttgt tagttataga tgtctaggta cttcaggggc acttcattga gagttttgtc    4920
aatgtctttt gaatattccc aagcccatga gtccttgaaa atatttttta tatatacagt    4980
aactttatgt gtaaatacat aagcggcgta agtttaaagg atgttggtgt tccacgtgtt    5040
ttattcctgt atgttgtcca attgttgaca gttctgaaga attc                     5084
```

<210> SEQ ID NO 2
<211> LENGTH: 976
<212> TYPE: PRT
<213> ORGANISM: Homo sapiens
<220> FEATURE:
<223> OTHER INFORMATION: human v-kit Hardy-Zuckerman 4 feline sarcoma
      viral oncogene homolog (c-kit, KIT), mast/stem cell
      growth factor receptor (SCFR), PBT, CD117, YB5.B8
      antigen

<400> SEQUENCE: 2

Met Arg Gly Ala Arg Gly Ala Trp Asp Phe Leu Cys Val Leu Leu Leu
 1               5                  10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn

```
                65                  70                  75                  80
            Glu Trp Ile Thr Glu Lys Ala Glu Ala Thr Asn Thr Gly Lys Tyr Thr
                            85                  90                  95

Cys Thr Asn Lys His Gly Leu Ser Asn Ser Ile Tyr Val Phe Val Arg
                        100                 105                 110

Asp Pro Ala Lys Leu Phe Leu Val Asp Arg Ser Leu Tyr Gly Lys Glu
                        115                 120                 125

Asp Asn Asp Thr Leu Val Arg Cys Pro Leu Thr Asp Pro Glu Val Thr
                    130                 135                 140

Asn Tyr Ser Leu Lys Gly Cys Gln Gly Lys Pro Leu Pro Lys Asp Leu
            145                 150                 155                 160

Arg Phe Ile Pro Asp Pro Lys Ala Gly Ile Met Ile Lys Ser Val Lys
                            165                 170                 175

Arg Ala Tyr His Arg Leu Cys Leu His Cys Ser Val Asp Gln Glu Gly
                        180                 185                 190

Lys Ser Val Leu Ser Glu Lys Phe Ile Leu Lys Val Arg Pro Ala Phe
                        195                 200                 205

Lys Ala Val Pro Val Val Ser Val Ser Lys Ala Ser Tyr Leu Leu Arg
                    210                 215                 220

Glu Gly Glu Glu Phe Thr Val Thr Cys Thr Ile Lys Asp Val Ser Ser
            225                 230                 235                 240

Ser Val Tyr Ser Thr Trp Lys Arg Glu Asn Ser Gln Thr Lys Leu Gln
                            245                 250                 255

Glu Lys Tyr Asn Ser Trp His His Gly Asp Phe Asn Tyr Glu Arg Gln
                        260                 265                 270

Ala Thr Leu Thr Ile Ser Ser Ala Arg Val Asn Asp Ser Gly Val Phe
                    275                 280                 285

Met Cys Tyr Ala Asn Asn Thr Phe Gly Ser Ala Asn Val Thr Thr Thr
                        290                 295                 300

Leu Glu Val Val Asp Lys Gly Phe Ile Asn Ile Phe Pro Met Ile Asn
            305                 310                 315                 320

Thr Thr Val Phe Val Asn Asp Gly Glu Asn Val Asp Leu Ile Val Glu
                            325                 330                 335

Tyr Glu Ala Phe Pro Lys Pro Glu His Gln Gln Trp Ile Tyr Met Asn
                        340                 345                 350

Arg Thr Phe Thr Asp Lys Trp Glu Asp Tyr Pro Lys Ser Glu Asn Glu
                    355                 360                 365

Ser Asn Ile Arg Tyr Val Ser Glu Leu His Leu Thr Arg Leu Lys Gly
                        370                 375                 380

Thr Glu Gly Gly Thr Tyr Thr Phe Leu Val Ser Asn Ser Asp Val Asn
            385                 390                 395                 400

Ala Ala Ile Ala Phe Asn Val Tyr Val Asn Thr Lys Pro Glu Ile Leu
                            405                 410                 415

Thr Tyr Asp Arg Leu Val Asn Gly Met Leu Gln Cys Val Ala Ala Gly
                        420                 425                 430

Phe Pro Glu Pro Thr Ile Asp Trp Tyr Phe Cys Pro Gly Thr Glu Gln
                    435                 440                 445

Arg Cys Ser Ala Ser Val Leu Pro Val Asp Val Gln Thr Leu Asn Ser
                        450                 455                 460

Ser Gly Pro Pro Phe Gly Lys Leu Val Val Gln Ser Ser Ile Asp Ser
            465                 470                 475                 480

Ser Ala Phe Lys His Asn Gly Thr Val Glu Cys Lys Ala Tyr Asn Asp
                            485                 490                 495
```

```
Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
            515                 520                 525

Phe Val Ile Val Ala Gly Met Met Cys Ile Ile Val Met Ile Leu Thr
            530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
            565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
            595                 600                 605

Tyr Gly Leu Ile Lys Ser Asp Ala Ala Met Thr Val Ala Val Lys Met
            610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
            645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
            690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                    725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
            770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                    805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
            850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
            885                 890                 895

Ala Glu Met Tyr Asp Ile Met Lys Thr Cys Trp Asp Ala Asp Pro Leu
            900                 905                 910
```

-continued

```
Lys Arg Pro Thr Phe Lys Gln Ile Val Gln Leu Ile Glu Lys Gln Ile
            915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 3
<211> LENGTH: 1782
<212> TYPE: DNA
<213> ORGANISM: Homo sapiens
<220> FEATURE:
<223> OTHER INFORMATION: protein-tyrosine phosphatase, non-receptor type
      11 (PTPN11), src homology 2 (SH2)-containing tyrosine phosphatase
      (SHP-2, SHP2, SH-PTP2), Noonan syndrome 1 (NS1), protein-tyrosine
      phosphatase 2C (PTP2C), CFC, BPTP3, PTP1D, MGC14433

<400> SEQUENCE: 3
atgacatcgc ggagatggtt tcacccaaat atcactggtg tggaggcaga aaacctactg     60
ttgacaagag gagttgatgg cagttttttg gcaaggccta gtaaaagtaa ccctggagac    120
ttcacacttt ccgttagaag aaatggagct gtcacccaca tcaagattca gaacactggt    180
gattactatg acctgtatgg aggggagaaa tttgccactt ggctgagtt ggtccagtat    240 tacatggaac atcacgggca attaaaagag aagaatggag atgtcattga gcttaaatat    300
cctctgaact gtgcagatcc tacctctgaa aggtggtttc atggacatct ctctgggaaa    360
gaagcagaga attattaac tgaaaaagga aaacatggta gttttcttgt acgagagagc    420
cagagccacc ctggagattt tgttcttttc tgtgcgcactg tgatgacaa aggggagagc    480 aatgacggca agtctaaagt gacccatgtt atgattcgct gtcaggaact gaaatacgac    540
gttggtggag gaaacggtt tgattctttg acagatcttg tggaacatta taagaagaat    600
cctatggtgg aaacattggg tacagtacta caactcaagc agcccttaa cacgactcgt    660 ataaatgctg ctgaaatag aagcagagtt cgagaactaa gcaaattagc tgagaccaca    720
gataaagtca acaaggctt tgggaagaa tttgagacac tacaacaaca ggagtgcaaa    780
cttctctaca gccgaaaaga gggtcaaagg caagaaaaca aaaacaaaaa tagatataaa    840
aacatcctgc cctttgatca taccagggtt gtcctacacg atggtgatcc caatgagcct    900
gtttcagatt acatcaatgc aaatatcatc atgcctgaat ttgaaaccaa gtgcaacaat    960
tcaaagccca aaaagagtta cattgccaca caaggctgcc tgcaaaacac ggtgaatgac   1020
ttttggcgga tggtgttcca agaaaactcc cgagtgattg tcatgacaac gaaagaagtg   1080
gagagaggaa agagtaaatg tgtcaaatac tggcctgatg agtatgctct aaaagaatat   1140
ggcgtcatgc gtgttaggaa cgtcaaagaa agcgccgctc atgactatac gctaagagaa   1200
cttaaacttt caaaggttgg acaagggaat acggagagaa cggtctggca ataccacttt   1260
cggacctggc cggaccacgg cgtgcccagc gaccctgggg gcgtgctgga cttcctggag   1320
gaggtgcacc ataagcagga gagcatcatg gatgcagggc cggtcgtggt gcactgcagt   1380
gctggaattg gccggacagg gacgttcatt gtgattgata ttcttattga catcatcaga   1440
gagaaaggtg ttgactgcga tattgacgtt cccaaaacca tccagatggt gcggtctcag   1500
aggtcaggga tggtccagac agaagcacag taccgattta tctatatggc ggtccagcat   1560
tatattgaaa cactacagcg caggattgaa gaagagcaga aaagcaagag gaaagggcac   1620
```

-continued

```
gaatatacaa atattaagta ttctctagcg gaccagacga gtggagatca gagccctctc    1680
ccgccttgta ctccaacgcc accctgtgca gaaatgagag aagacagtgc tagagtctat    1740
gaaaacgtgg gcctgatgca acagcagaaa agtttcagat ga                      1782
```

<210> SEQ ID NO 4
<211> LENGTH: 593
<212> TYPE: PRT
<213> ORGANISM: Homo sapiens
<220> FEATURE:
<223> OTHER INFORMATION: protein-tyrosine phosphatase, non-receptor type 11 (PTPN11), src homology 2 (SH2)-containing tyrosine phosphatase (SHP-2, SHP2, SH-PTP2), Noonan syndrome 1 (NS1), protein-tyrosine phosphatase 2C (PTP2C), CFC, BPTP3, PTP1D

<400> SEQUENCE: 4

```
Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320
```

```
Ser Lys Pro Lys Lys Ser Tyr Ile Ala Thr Gln Gly Cys Leu Gln Asn
            325                 330                 335

Thr Val Asn Asp Phe Trp Arg Met Val Phe Gln Glu Asn Ser Arg Val
        340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
        370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
        435                 440                 445

Ile Met Asp Ala Gly Pro Val Val His Cys Ser Ala Gly Ile Gly
        450                 455                 460

Arg Thr Gly Thr Phe Ile Val Ile Asp Ile Leu Ile Asp Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
        515                 520                 525

Ile Glu Glu Glu Gln Lys Ser Lys Arg Lys Gly His Glu Tyr Thr Asn
530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
                565                 570                 575

Ala Arg Val Tyr Glu Asn Val Gly Leu Met Gln Gln Gln Lys Ser Phe
            580                 585                 590

Arg

<210> SEQ ID NO 5
<211> LENGTH: 23
<212> TYPE: DNA
<213> ORGANISM: Artificial Sequence
<220> FEATURE:
<223> OTHER INFORMATION: synthetic siRNP target 23-nt sequence motif
<221> NAME/KEY: modified_base
<222> LOCATION: (3)...(21)
<223> OTHER INFORMATION: n = g, a, c or t

<400> SEQUENCE: 5
aannnnnnnn nnnnnnnnnn ntt                                          23

<210> SEQ ID NO 6
<211> LENGTH: 22
<212> TYPE: DNA
<213> ORGANISM: Artificial Sequence
<220> FEATURE:
<223> OTHER INFORMATION: synthetic SHP2 exon 3a PCR amplification
      forward primer

<400> SEQUENCE: 6
```

```
gtaaaatccg acgtggaaga tg                                              22
```

<210> SEQ ID NO 7
<211> LENGTH: 24
<212> TYPE: DNA
<213> ORGANISM: Artificial Sequence
<220> FEATURE:
<223> OTHER INFORMATION: synthetic SHP2 exon 3a PCR amplification
      reverse primer

<400> SEQUENCE: 7

```
gttcagaggt aggatctgca cagt                                            24
```

<210> SEQ ID NO 8
<211> LENGTH: 23
<212> TYPE: DNA
<213> ORGANISM: Artificial Sequence
<220> FEATURE:
<223> OTHER INFORMATION: synthetic SHP2 exon 3b PCR amplification
      forward primer

<400> SEQUENCE: 8

```
gaaatggagc tgtcacccac atc                                             23
```

<210> SEQ ID NO 9
<211> LENGTH: 23
<212> TYPE: DNA
<213> ORGANISM: Artificial Sequence
<220> FEATURE:
<223> OTHER INFORMATION: synthetic SHP2 exon 3b PCR amplification
      reverse primer

<400> SEQUENCE: 9

```
catacacaga ccgtcatgca ttt                                             23
```

<210> SEQ ID NO 10
<211> LENGTH: 23
<212> TYPE: DNA
<213> ORGANISM: Artificial Sequence
<220> FEATURE:
<223> OTHER INFORMATION: synthetic SHP2 exon 4a PCR amplification
      forward primer

<400> SEQUENCE: 10

```
tttgtgaaag aacaacatga acc                                             23
```

<210> SEQ ID NO 11
<211> LENGTH: 20
<212> TYPE: DNA
<213> ORGANISM: Artificial Sequence
<220> FEATURE:
<223> OTHER INFORMATION: synthetic SHP2 exon 4a PCR amplification
      reverse primer

<400> SEQUENCE: 11

```
gacttgccgt cattgctctc                                                 20
```

<210> SEQ ID NO 12
<211> LENGTH: 26
<212> TYPE: DNA
<213> ORGANISM: Artificial Sequence
<220> FEATURE:
<223> OTHER INFORMATION: synthetic SHP2 exon 4b PCR amplification
      forward primer

<400> SEQUENCE: 12

```
ggaaaacatg gtagttttct tgtacg                                          26
```

<210> SEQ ID NO 13
<211> LENGTH: 25
<212> TYPE: DNA
<213> ORGANISM: Artificial Sequence
<220> FEATURE:
<223> OTHER INFORMATION: synthetic SHP2 exon 4b PCR amplification
      reverse primer

<400> SEQUENCE: 13
tgaatgtaat ggtgtctgtc ttctg                                25

<210> SEQ ID NO 14
<211> LENGTH: 19
<212> TYPE: DNA
<213> ORGANISM: Artificial Sequence
<220> FEATURE:
<223> OTHER INFORMATION: synthetic SHP2 exon 7 PCR amplification forward
      primer

<400> SEQUENCE: 14
gtaatgctga tccaggctt                                       19

<210> SEQ ID NO 15
<211> LENGTH: 21
<212> TYPE: DNA
<213> ORGANISM: Artificial Sequence
<220> FEATURE:
<223> OTHER INFORMATION: synthetic SHP2 exon 7 PCR amplification reverse
      primer

<400> SEQUENCE: 15
ccctgaggaa aggtacagag g                                    21

<210> SEQ ID NO 16
<211> LENGTH: 21
<212> TYPE: DNA
<213> ORGANISM: Artificial Sequence
<220> FEATURE:
<223> OTHER INFORMATION: synthetic SHP2 exon 8 PCR amplification forward
      primer

<400> SEQUENCE: 16
gctggggagt aactgatttg a                                    21

<210> SEQ ID NO 17
<211> LENGTH: 20
<212> TYPE: DNA
<213> ORGANISM: Artificial Sequence
<220> FEATURE:
<223> OTHER INFORMATION: synthetic SHP2 exon 8 PCR amplification reverse
      primer

<400> SEQUENCE: 17
ctttcaggac atgaggaagg                                      20

<210> SEQ ID NO 18
<211> LENGTH: 26
<212> TYPE: DNA
<213> ORGANISM: Artificial Sequence
<220> FEATURE:
<223> OTHER INFORMATION: synthetic SHP2 exon 13a PCR amplification
      forward primer

<400> SEQUENCE: 18
gtccactaaa agttgtgcat taaaca                               26

```
<210> SEQ ID NO 19
<211> LENGTH: 20
<212> TYPE: DNA
<213> ORGANISM: Artificial Sequence
<220> FEATURE:
<223> OTHER INFORMATION: synthetic SHP2 exon 13a PCR amplification
      reverse primer

<400> SEQUENCE: 19
caggctggta cctgctcttc                                                   20

<210> SEQ ID NO 20
<211> LENGTH: 22
<212> TYPE: DNA
<213> ORGANISM: Artificial Sequence
<220> FEATURE:
<223> OTHER INFORMATION: synthetic SHP2 exon 13b PCR amplification
      forward primer

<400> SEQUENCE: 20
catgatgttt ccttcgtagg tg                                                22

<210> SEQ ID NO 21
<211> LENGTH: 20
<212> TYPE: DNA
<213> ORGANISM: Artificial Sequence
<220> FEATURE:
<223> OTHER INFORMATION: synthetic SHP2 exon 13b PCR amplification
      reverse primer

<400> SEQUENCE: 21
ctcctgctca aaaggagagc                                                   20

<210> SEQ ID NO 22
<211> LENGTH: 18
<212> TYPE: DNA
<213> ORGANISM: Artificial Sequence
<220> FEATURE:
<223> OTHER INFORMATION: synthetic PCR amplification M13 forward primer

<400> SEQUENCE: 22
tgtaaaacga cggccagt                                                     18

<210> SEQ ID NO 23
<211> LENGTH: 23
<212> TYPE: DNA
<213> ORGANISM: Artificial Sequence
<220> FEATURE:
<223> OTHER INFORMATION: synthetic PCR amplification M13 reverse primer

<400> SEQUENCE: 23
agcggataac aatttcacac agg                                               23
```